US007411100B2

(12) United States Patent
Pauluth et al.

(10) Patent No.: US 7,411,100 B2
(45) Date of Patent: Aug. 12, 2008

(54) PROCESS FOR THE PREPARATION OF RING COMPOUNDS

(75) Inventors: Detlef Pauluth, Ober-Ramstadt (DE); Peer Kirsch, Seeheim-Jugenheim (DE); Peter Baeuerle, Thalfingen (DE); Oliver Deeg, Wachenheim a.d.W. (DE)

(73) Assignee: Merck GmbH, Darmstadt (DE)

( * ) Notice: Subject to any disclaimer, the term of this patent is extended or adjusted under 35 U.S.C. 154(b) by 127 days.

(21) Appl. No.: 11/437,608

(22) Filed: May 22, 2006

(65) Prior Publication Data

US 2006/0216754 A1 Sep. 28, 2006

Related U.S. Application Data

(62) Division of application No. 10/388,607, filed on Mar. 17, 2003, now Pat. No. 7,183,447.

(30) Foreign Application Priority Data

Mar. 15, 2002 (DE) ................................ 102 11 597

(51) Int. Cl.

| | |
|---|---|
| ***C07C 25/13*** | (2006.01) |
| ***C07C 205/00*** | (2006.01) |
| ***C07C 233/00*** | (2006.01) |
| ***C07C 63/00*** | (2006.01) |
| ***C07C 255/00*** | (2006.01) |

(52) U.S. Cl. ......................... 570/131; 570/237; 568/39; 568/424; 568/426; 564/152; 562/480; 558/357

(58) Field of Classification Search ....................... None
See application file for complete search history.

(56) References Cited

U.S. PATENT DOCUMENTS

| | | | |
|---|---|---|---|
| 4,841,009 | A | 6/1989 | Kelsey |
| 5,756,804 | A | 5/1998 | Haber et al. |
| 5,919,930 | A | 7/1999 | Haber et al. |
| 6,307,087 | B1 | 10/2001 | Buchwald et al. |

FOREIGN PATENT DOCUMENTS

| | | | |
|---|---|---|---|
| DE | 42 20 082 | | 12/1993 |
| DE | 44 26 671 | A1 | 2/1996 |
| DE | 199 33 175 | | 1/2000 |
| DE | 198 58 594 | | 6/2000 |
| DE | 102 11 597 | | 10/2003 |
| EP | 0 470 795 | A1 | 2/1992 |
| EP | 0 730 019 | | 9/1996 |
| EP | 0 903 391 | | 3/1999 |
| EP | 0 959 060 | | 11/1999 |
| EP | 1 346 995 | | 9/2003 |
| GB | 22 40 778 | | 8/1991 |
| GB | 2 367 058 | | 3/2002 |
| WO | WO 89 02 425 | | 3/1989 |
| WO | WO 89 02425 | | 3/1989 |
| WO | WO 90 01526 | | 2/1990 |
| WO | WO 91 05 029 | | 4/1991 |
| WO | WO 98 45 265 | | 10/1998 |

OTHER PUBLICATIONS

Tovar et al., "Exploiting the versatility of organometallic cross-coupling reactions for entry into extended aromatic systems", Journal of Organometallic Chemistry, vol. 653 (2002) pp. 215-222.

Goldfinger et al., Directed Electrophilic Cyclizations: Efficient Methodology for the Synthesis of Fused Polycyclic Aromatics, Journal of the American Chemical Society, 1997, vol. 119, p. 4578-4593).

Partial European International Search Report dated Jul. 28, 2003 issued in EP 1 346 995.

O. Deeg, et al., "Combinatorial parallel synthesis and automated screening of a novel class of liquid cyrstalline materiasl", The Royal Society of Chemistry, 2002, pp. 2762-2763.

Kiryanov, et al., "Synthesis and mesomorphic properties of 1,1-difluoroalkyl- . . . ", J. Mater. Chem., 2001, 11, pp. 3068-3077.

M. Hird, et al., "Novel liquid crystals with a bent molecular shape containing a 1,5- . . . " J. Mater. Chem., 2001, 11, pp. 2732-2742.

P. L. Coe., et al., "Electrophilic ipso substitution of trimethylsilyl groups in fluorobenzenes", Journal of Fluorine Chemistry 92, (1998), pp. 27-32.

B. Bennetau, et al., "Fonctionnalisation régiosélective en position 2 de benzenes 1,3-disubstitués", Tetrahedron vol. 49, No. 47, 1993, pp. 10843-10854.

H.. G. Alt, et al., "Syndiospezifische Polymerisation von Propylen: 2-und . . . ", Journal of Organometallic Chemistry, 522, (1996), pp. 39-54.

V. Hensel, et al., "Building Blocks for the Construction of Large Chloro-Functionalized, Hexagonal Oligophenylene Cycles", Eur. J. Org. Chem., 1999, pp. 451-458.

Caplus Database, XP-002247824, J. Frahn et al, 1997.

Caplus Database. XP-002247825, V. Hensel, et al, 1997.

Caplus Database, XP-002247826, D. Kaufman, 1987.

X. Deng, "An efficient convergent synthesis of novel anisotropic adsorbates based on nanometer-sized and tripod-shaped oligophenylenes end-capped with triallylsilyl groups," J. Org.Chem. 2002, 67, pp. 5279-5283.

Japanese Abstract No. 08 081416 dated Mar. 26, 1996.

Japanese Abstract No. 02 308114 dated Dec. 21, 1990.

*Primary Examiner*—Sikarl A. Witherspoon
(74) *Attorney, Agent, or Firm*—Millen, White, Zelano, Branigan, P.C.

(57) ABSTRACT

In a process for the preparation of ring compounds via a combinatorial synthesis, the reaction procedure is based on a Suzuki coupling, subsequent halo-demetallation and finally a further Suzuki coupling. The Suzuki couplings are each carried out with a boronic acid or a boronic acid ester. The reaction procedure uses provides novel ring compounds and uses novel synthesis units used for this purpose. The novel ring compounds are suitable for use as constituents in liquid-crystalline mixtures.

13 Claims, No Drawings

PROCESS FOR THE PREPARATION OF RING COMPOUNDS

This application is a divisional of U.S. Ser. No. 10/388,607, filed Mar. 17, 2003 now U.S Pat. No. 7,183,447.

The present invention relates to a process for the preparation of ring compounds via a combinatorial synthesis based on a Suzuki coupling, subsequent halo-demetallation and finally a Suzuki coupling. The Suzuki couplings are each carried out with a boronic acid or a boronic acid ester. The present invention likewise relates to the corresponding ring compounds and to the novel synthesis units used for this purpose. The ring compounds according to the invention are preferably used as constituents in liquid-crystalline mixtures.

The prior art discloses the palladium-catalysed cross-coupling reaction of aromatic boron compounds, such as boronic acids and derivatives thereof, and aromatic halogen compounds (EP 0 470 795 A1), which has for some years also increasingly been used in the area of organic synthesis. The process described in EP 0 470 795 A1 is based on a homogeneously catalysed process using palladium(0) complexes, in particular tetrakis(triphenylphosphine)palladium(0). It is disadvantageous in this process that the complexes are oxidation-sensitive, causing them to lose activity. Owing to the varying activity, the process is difficult to reproduce and the yields are in some cases very low. In addition, the complexes are very expensive.

DE 44 26 671 A1 discloses a process for the preparation of polycyclic aromatic compounds by cross-coupling aromatic boron compounds with aromatic halogen compounds or perfluoroalkyl sulfonates with palladium catalysis in the presence of at least one water-soluble complex ligand. This process is carried out with a 2-phase system comprising an organic phase and an aqueous phase; with the palladium catalyst being dissolved in the organic phase. It is disadvantageous in this process that very good mixing of the two phases is a prerequisite for the reaction. In addition, this process is also very expensive owing to the catalysts employed.

Starting from this prior art, an object of the present invention is to provide a process or to develop a combinatorial synthesis strategy with which products can be obtained in high yield and high conversion with a small number of reaction steps.

Upon further study of the specification and appended claims, further objects and advantages of this invention will become apparent to those skilled in the art.

These objects are achieved in accordance with the invention by a process comprising subjecting a compound of formulae V to VIII

V

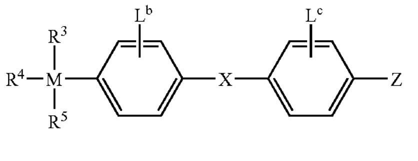

-continued

VI

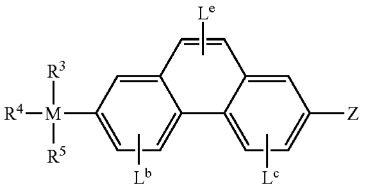

VII

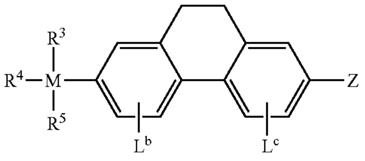

VIII

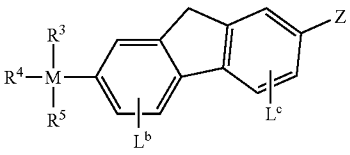

wherein

Z is I, Cl, Br or triflate,

M is Si, Ge or Sn, and $R^3$, $R^4$ and $R^5$, independently of one another, are identical or different and are each H, $C_1$-$C_{12}$-alkyl or $C_1$-$C_{12}$-alkoxy, via combinatorial synthesis, to the following reaction steps which are carried out in a matrix-like arrangement of reaction vessels:

A) Suzuki coupling with a boronic acid or a boronic acid ester of formula X

X

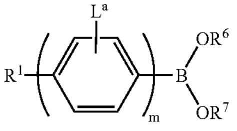

wherein $R^6$ and $R^7$, independently of one another, are identical or different and are each H, $C_1$-$C_{12}$-alkyl, $C_2$-$C_{12}$-alkenyl or aryl, and where $R^6$ and $R^7$ can also be bridged in a cyclic manner;

B) subsequent halo-demetallation; and

C) Suzuki coupling with a boronic acid or a boronic acid ester of formula XI

XI

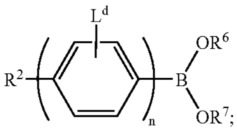

wherein one or two CH groups in the aromatic ring systems of formulae V to VII, X and XI may each also be replaced by N.

The invention further relates to liquid-crystalline ring compounds of formula XIII

XIII

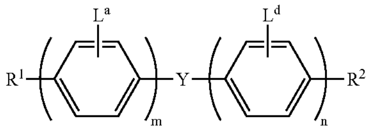

wherein one or two CH groups in the aromatic ring systems of formula XIII may each be replaced by N;

Y is a group of formulae XIV to XVII

XIV

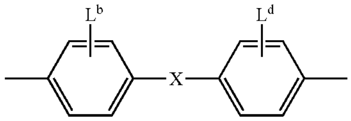

XV

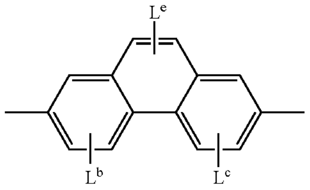

XVI

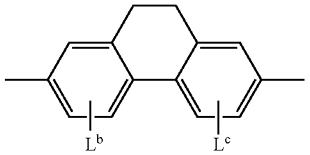

XVII

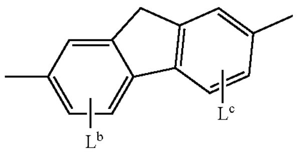

in which one or two CH groups in the aromatic ring systems may each be replaced by N;

m and n, independently of one another, are identical or different and are each 0 or 1, and the sum m+n is 1 or 2;

X is a single bond, —$CH_2$—$CH_2$—, —CH═CH—, —C≡C— or

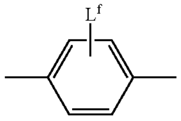

L, independently of one another, are identical or different and are each R, F, Cl, Br, I, OH, OR, SH, SR, CN, $NO_2$, NO, CHO, COOH, COOR, $CONH_2$, CONHR, $CONR_2$, $CF_3$, $NH_2$, NHR or $NR_2$;

R is an alkyl, alkenyl or acyl group having up to 12 carbon atoms or an aryl group having 6 carbon atoms which is optionally substituted by an alkyl group having from 1 to 12 carbon atoms; and a, b, c, d, e and f, independently of one another, are identical or different and are each 0, 1 or 2, and the sum a+b+c+d+e+f is 1 to 8, preferably 3 to 8;

$R^1$ and $R^2$, independently of one another, are identical or different and are each H, F, Cl, CN, NCS, a straight-chain or branched, optionally chiral alkyl radical or alkoxy radical having from 1 to 12 carbon atoms or an alkenyl radical or alkynyl radical having from 2 to 8 carbon atoms, in each of which, in addition, one $CH_2$ group may be replaced by —O—, —CO—, —O—CO—, —COO— or —CH═CH— in such a way that heteroatoms are not linked directly to one another and/or one or more H may be replaced by halogen, preferably F; and in the case where m is 0 or n is 0, one $CH_2$ group in $R^1$ or $R^2$ may be replaced by one of the following groups:

a) trans-1,4-cyclohexylene, in which, in addition, one or more non-adjacent $CH_2$ groups may each be replaced by —O— or —S—, b) a radical from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl, or c) 1,4-cyclohexenylene, and in which the radicals a), b) and c) may also be substituted by CN and/or halogen.

In accordance with a further aspect of the invention there are provide boronic acids or boronic acid ester compounds as synthesis units, including:

boronic acid or boronic acid ester compounds of formula XIX

XIX

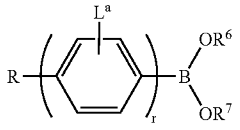

wherein one or two CH groups in the aromatic ring system may each be replaced by N;

r is 1 or 2;

R is H, F, Cl, CN, NCS, a straight-chain or branched, optionally chiral, alkyl radical or alkoxy radical having from 1 to 12 carbon atoms or an alkenyl radical or alkynyl radical having from 2 to 8 carbon atoms, in each of which, in addition, one $CH_2$ group may be replaced by —O—, —CO—, —O—CO— or —COO— in such a way that heteroatoms are not linked directly to one another and/or one or more H may be replaced by halogen;

the L groups, independently of one another, are identical or different and are each R', F, Cl, Br, I, OH, OR', SH, SR', CN, $NO_2$, NO, CHO, COOH, COOR', $CONH_2$, CONHR', $CONR_2$', $CF_3$, $NH_2$, NHR' or $NR_2$';

R' is an alkyl, alkenyl or acyl group having from up to 12 carbon atoms or an aryl group having 6 carbon atoms, which is optionally substituted by an alkyl group having from 1 to 12 carbon atoms;

a, is 0, 1 or 2;

$R^6$ and $R^7$, independently of one another, are identical or different and are each H, $C_1$-$C_{12}$-alkyl, $C_2$-$C_{12}$-alkenyl or aryl, and where $R^6$ and $R^7$ can also be bridged in a cyclic manner; and boronic acid or boronic acid ester compound of formula XXI

XXI

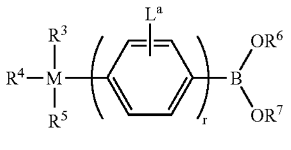

wherein one or two CH groups in the aromatic ring system may each be replaced by N;

r is 1 or 2;

$R^3$, $R^4$ and $R^5$, independently of one another, are identical or different and are each H, $C_1$-$C_{12}$-alkyl or $C_1$-$C_{12}$-alkoxy;

$R^6$ and $R^7$, independently of one another, are identical or different and are each H, $C_1$-$C_{12}$-alkyl, $C_2$-$C_{12}$-alkenyl or aryl, and where $R^6$ and $R^7$ can also be bridged in a cyclic manner;

M is Si, Ge or Sn;

the L groups, independently of one another, are identical or different and are each R', F, Cl, Br, I, OH, OR', SH, SR', CN, $NO_2$, NO, CHO, COOH, COOR', $CONH_2$, CONHR', $CONR_2$', $CF_3$, $NH_2$, NHR' or $NR_2$';

R' is an alkyl, alkenyl or acyl group having from up to 12 carbon atoms or an aryl group having 6 carbon atoms, which is optionally substituted by an alkyl group having from 1 to 12 carbon atoms; and a, is 0, 1 or 2.

In accordance with the invention, a process is provided for the preparation of ring compounds of the general formulae I to IV

I

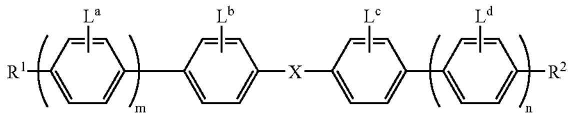

II

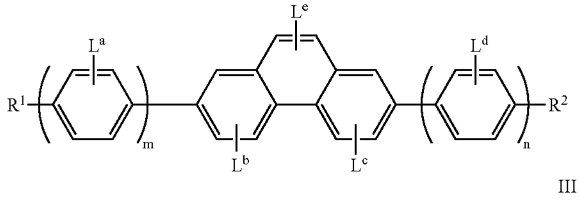

III

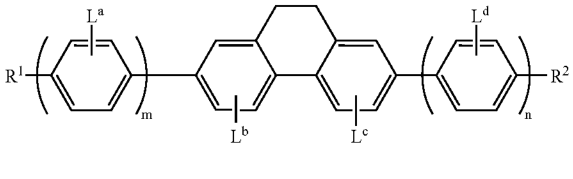

-continued

IV

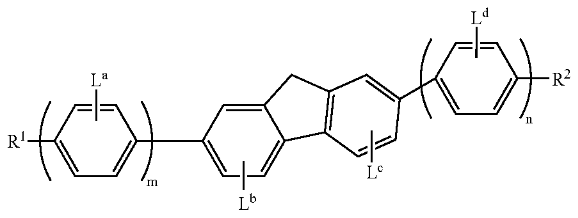

In these formulae, m and n, independently of one another, are identical or different and can adopt the values 0 or 1, where the sum (m+n) is 1 or 2. Particularly preferably, m=n=1, i.e. the sum (m+n)=2.

X is a single bond, $-CH_2-CH_2-$, $-CH=CH-$, $-C\equiv C-$ or

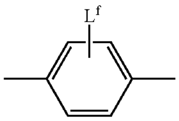

X is preferably a single bond.

The L groups, independently of one another, are identical or different and are each R, F, Cl, Br, I, OH, OR, SH, SR, CN, $NO_2$, NO, CHO, COOH, COOR, $CONH_2$, CONHR, $CONR_2$, $CF_3$, $NH_2$, NHR or $NR_2$, where R is an alkyl, alkenyl or acyl group having from 1 to 12 carbon atoms or an aryl group having 6 carbon atoms, which may, if desired, in turn be substituted by an alkyl group having from 1 to 12 carbon atoms. The L groups are preferably, independently of one another, identical or different, and are each F, Cl, $CF_3$ or $CH_3$, where F is particularly preferred.

The indices a, b, c, d, e and f may, independently of one another, be identical or different and adopt the values 0, 1 or 2, where the sum a+b+c+d+e+f adopts values between 1 and 8, preferably between 3 and 8 and particularly preferably between 4 and 8. One or two CH groups in the aromatic ring systems of the formulae I to IV may each be replaced by N.

$R^1$ and $R^2$, independently of one another, are identical or different and are H, F, Cl, CN or NCS. It is likewise possible for $R^1$ and/or $R^2$ to be a straight-chain or branched, optionally chiral alkyl radical or alkoxy radical having from 1 to 12 carbon atoms or an alkenyl radical or alkynyl radical having from 2 to 8 carbon atoms, where one $CH_2$ group in each of these organic radicals may also be replaced by $-O-$, $-CO-$, $-O-CO-$ or $-COO-$ in such a way that heteroatoms are not linked directly to one another and/or one or more H may be replaced by halogen, preferably F. $R^1$ and/or $R^2$ are preferably a straight-chain alkyl radical having from 1 to 7 carbon atoms. In a further preferred embodiment, $R^2$ is a chiral alkyl radical having from 1 to 12 carbon atoms.

In the case where m=0 or n=0, one $CH_2$ group in $R^1$ or $R^2$ is preferably replaced by one of the following groups:

a) trans-1,4-cyclohexylene, in which, in addition, one or more non-adjacent $CH_2$ groups may each be replaced by $-O-$ or $-S-$, b) a radical from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl, or c) 1,4-cyclohexenylene.

The radicals a), b) and c) may also be substituted by CN and/or halogen.

If $R^1$ and/or $R^2$ in the formulae above and below are an alkyl radical, this may be straight-chain or branched. It is particularly preferably straight-chain, has 1, 2, 3, 4, 5, 6 or 7 carbon atoms and is accordingly methyl, ethyl, propyl, butyl, pentyl, hexyl or heptyl, furthermore octyl, nonyl, decyl, undecyl or dodecyl.

If $R^1$ and/or $R^2$ are an alkyl radical in which one $CH_2$ group has been replaced by —O—, this may be straight-chain or branched. It is preferably straight-chain and has from 1 to 10 carbon atoms. The first $CH_2$ group in this alkyl radical is particularly preferably replaced by —O—, so that the radical $R^1$ attains the meaning alkoxy and is methoxy, ethoxy, propoxy, butoxy, pentyloxy, hexyloxy, heptyloxy, octyloxy or nonyloxy.

It is furthermore also possible for a $CH_2$ group elsewhere to be replaced by —O—, so that the radical $R^1$ and/or $R^2$ is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

If $R^1$ and/or $R^2$ are an alkyl radical in which one $CH_2$ group has been replaced by —O— and one has been replaced by —CO—, these are adjacent. These thus contain an acyloxy group —CO—O— or an oxycarbonyl group —O—CO—. These are particularly preferably straight-chain and have from 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl and 4-(methoxycarbonyl)butyl.

If $R^1$ and/or $R^2$ are an alkyl or alkenyl radical which is monosubstituted by CN or $CF_3$, this radical is preferably straight-chain and the substitution by CN or $CF_3$ is in the ω-position.

If $R^1$ and/or $R^2$ are an alkyl radical which is at least monosubstituted by halogen, this radical is preferably straight-chain. Halogen is preferably F or Cl. In the case of polysubstitution, halogen is preferably F. The resultant radicals also include perfluorinated radicals. In the case of monosubstitution, the fluorine or chlorine substituent can be in any desired position, but preferably in the ω-position.

Compounds of the formula I having a branched wing group $R^1$ and/or $R^2$ may occasionally be of importance owing to better solubility in the conventional liquid-crystalline base materials, but in particular as chiral dopants if they are optically active. Smectic compounds of this type are suitable as components of ferroelectric materials.

Branched groups of this type generally contain not more than one chain branch. Preferred branched radicals $R^1$ and/or $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentyloxy, 3-methylpentyloxy, 2-ethylhexyloxy, 1-methylhexyloxy and 1-methylheptyloxy.

The groups m, n, X, L, a, b, c, d, e, f, $R^1$ and $R^2$ below are as defined above unless expressly stated otherwise. Correspondingly, one or two CH groups in the ring systems mentioned below may also each be replaced by N analogously to the ring compounds of the general formulae I to IV.

The ring compounds of the general formulae I to IV are prepared starting from the compounds of the formulae V to VIII:

V

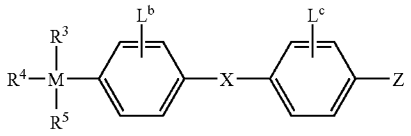

VI

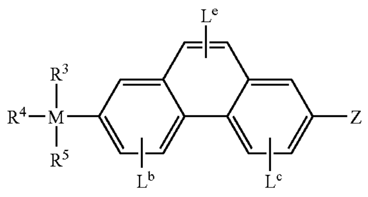

VII

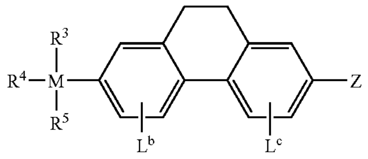

VIII

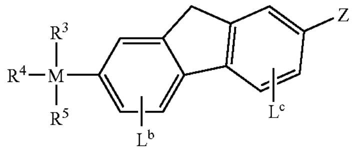

Z here is selected from the group consisting of I, Cl, Br and OTf (triflate), where Z is preferably 1, and M is selected from the group consisting of Si, Ge and Sn, where Si is preferred.

$R^3$, $R^4$ and $R^5$, independently of one another, are identical or different and are H, $C_1$-$C_{12}$-alkyl or $C_1$-$C_{12}$-alkoxy.

Furthermore, at least one of the radicals $R^3$, $R^4$ and $R^5$ in the general formulae V to VIII can be a fluorine-containing alkyl radical of the general formula IX $$—(CH_2)_p—(CF_2)_q—CF_3 \qquad \text{IX}$$

where p can adopt values in the range from 2 to 4, q can adopt values ≧2, and the sum (p+q) can adopt values in the range from 2 to 11. q is preferably >p.

$R^3$, $R^4$, $R^5$, M and Z below are as defined above unless expressly stated otherwise.

The ring compounds are prepared via combinatorial synthesis, in which the following reaction steps are carried out in a matrix-like arrangement of reaction vessels:

A) Suzuki coupling with a boronic acid or a boronic acid ester, preferably a boronic acid ester, of the general formula X

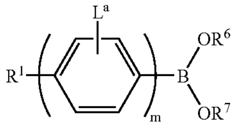

X where $R^6$ and $R^7$, independently of one another, are identical or different and are H, $C_1$-$C_{12}$-alkyl, $C_2$-$C_{12}$-alkenyl, preferably $C_3$-$C_{12}$-alkenyl, or $C_{6-10}$-aryl (preferably $C_6$-aryl). $R^6$ and $R^7$ may also be bridged in a cyclic manner.

$R^6$ and $R^7$ below are as defined above unless expressly stated otherwise.

B) subsequent halo-demetallation, preferably iodo-desilylation, and

C) Suzuki coupling with a boronic acid or a boronic acid ester, preferably a boronic acid ester, of the general formula XI

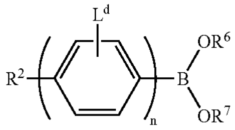

XI

In a step preceding step A), the compound of the formula V, in which X is a single bond, is preferably prepared from a boronic acid or a boronic acid ester of the formula XII

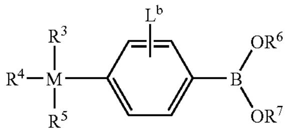

XII by Suzuki coupling with an at least partially fluorinated p-bromoiodo-benzene, which is carried out as a combinatorial synthesis in a matrix-like arrangement of reaction vessels, with a subsequent iodination step for substitution of the bromine, for example by means of butyllithium and an iodinating agent.

A particular advantage of the process according to the invention is that this is carried out as a combinatorial synthesis. For the development of combinatorial synthesis, it is necessary to develop a synthesis concept with reactions matched to one another, with the aim being to optimise the reactions with respect to conversion and yield. The process is carried out as a divergent synthesis, which has the advantage over a linear synthesis that only three reaction steps are needed. Linear synthesis, by contrast, would require five reaction steps. A further advantage is the smaller purification effort compared with the performance of a linear synthetic process.

The intermediates and/or end products are preferably purified by recrystallisation, and the crystals are isolated via cartridges for solid-phase extraction, with the purification being carried out in parallel for all reaction vessels.

Regarding the Suzuki couplings, the base needed for this purpose is preferably selected from the group consisting of the hydroxides, carbonates and fluorides, with barium hydroxide and caesium fluoride being particularly preferred.

The catalyst employed is preferably a palladium-containing compound, particularly preferably palladium acetate.

The reaction is preferably carried out in a polar solvent, such as, for example, an alcohol or ether. Particular preference is given here to the use of isopropanol.

In a further particularly preferred variant of the Suzuki coupling, the base employed is caesium fluoride, the catalyst employed is palladium acetate, and the solvent employed is dioxane.

The preferred Suzuki coupling variants described here have the advantage that virtually quantitative conversion is achieved and the product is free from palladium. At the same time, no by-products which cannot be separated off are formed, meaning that the purity of the crude products is adequate for the subsequent reactions. Further advantages of this catalyst are its simple handling, its stability in air and its low price.

The Suzuki couplings are preferably carried out at a temperature between 10 and 120° C. and a reaction duration between 0.1 and 30 hours. Particular preference is given to temperatures between 50 and 100° C. and a reaction duration between 18 and 24 hours.

The iodo-desilylation, as the preferred variant of the halo-demetallation, is preferably carried out with addition of iodine chloride in methyl cyanide. Temperatures between 10 and 75° C. and a reaction duration between 0.1 and 20 hours are preferably observed here. Particular preference is given to temperatures between 20 and 30° C. and a reaction duration between 0.5 and 2 hours.

An important step in the synthesis is suppression of side-chain chlorinations during the halo-demetallation. This side-chain chlorination of the radicals $R^1$ and $R^2$ can be prevented virtually completely if an iodo-desilylation is carried out in acetonitrile. A further reason for the preference for iodo-desilylation in combination with the Suzuki coupling is its compatibility with respect to fluorine substituents in the o-position.

The process according to the invention for the preparation of ring compounds of the general formulae I to IV is shown in detailed diagrammatic form below for the preferred ring compounds of the general formula XVIII.

The preparation of the biphenyl, the starting substance of the process according to the invention, is shown in scheme 1. Scheme 2 shows the synthesis of the terphenyl starting from the biphenyl from scheme 1 and a boronic acid (step A of the process according to the invention). Scheme 3 describes the iodo-desilylation of the terphenyl from scheme 2 (step B of the process according to the invention), and scheme 4 describes the synthesis of the quaterphenyl (step C of the process according to the invention).

Scheme 1

Synthesis of the biphenyl (8)

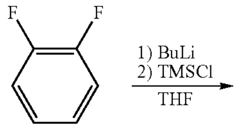

1

-continued
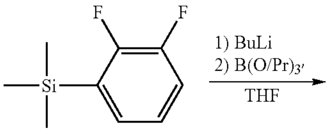
2 [91%]
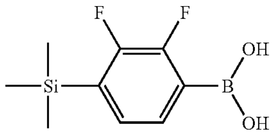
3 [78%]
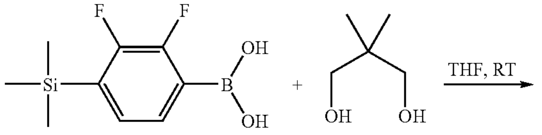
3 4
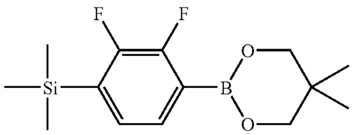
5 [100%]
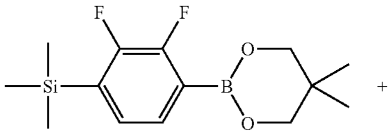
5
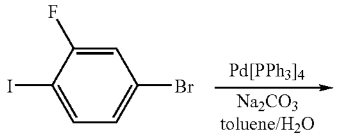
6
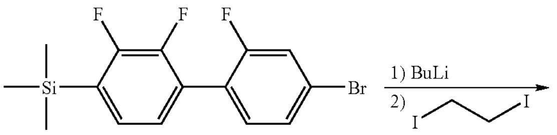
7 [88%]
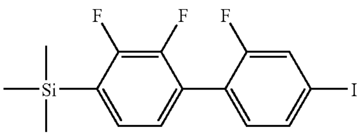
8 [84%]
Scheme 2
Synthesis of the terphenyl (10)
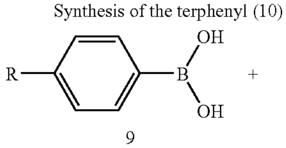
9
-continued
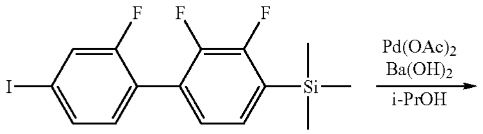
8
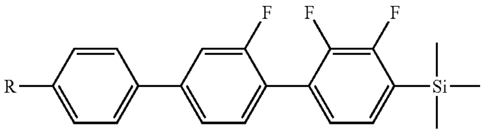
10
Scheme 3
Synthesis of the terphenyl (11) by iodo-desilyation
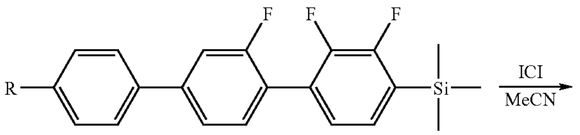
10
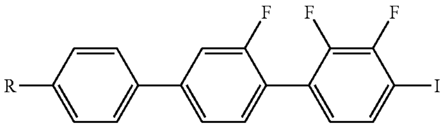
11
Scheme 4
Synthesis of the quaterphenyl (12)
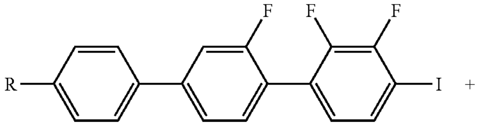
11
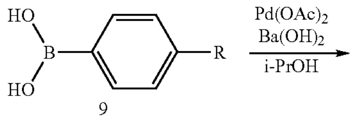
9
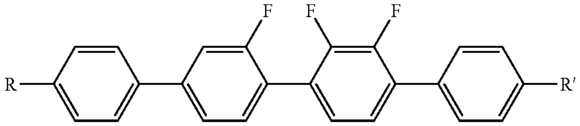
12
Ring compounds of the general formula XIII
XIII
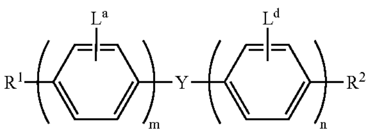

-continued where m and n, independently of one another, are identical or different and adopt the value of 0 or 1, where the sum (m + n) is 1 or 2, preferably m = n = 1, i.e. the sum (m + n) = 2, are likewise prepared in accordance with the invention.

Y here is a group of the general formulae XIV to XVII

XIV

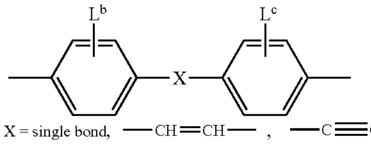

where X = single bond, —CH═CH— , —C≡C— or

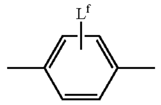

XV

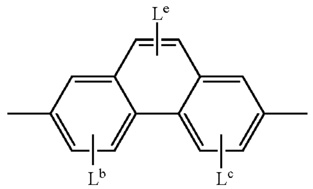

XVI

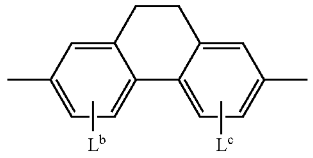

XVII

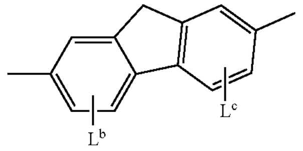

L, independently of one another, are identical or different and are R, F, Cl, Br, I, OH, OR, SH, SR, CN, $NO_2$, NO, CHO, COOH, COOR, $CONH_2$, CONHR, $CONR_2$, $CF_3$, $NH_2$, NHR or $NR_2$, where R is an alkyl, alkenyl or acyl group having from 1 to 12 carbon atoms or an aryl group having 6 carbon atoms, which may, if desired, in turn be substituted by an alkyl group having from 1 to 12 carbon atoms. L are preferably, independently of one another, identical or different, and are F, Cl, $CF_3$ or $CH_3$, where F is particularly preferred.

The indices a, b, c, d, e and f may, independently of one another, be identical or different and adopt the values 0, 1 or 2, where the sum (a+b+c+d+e+f adopts values between 1 and 8, preferably between 3 and 8 and particularly preferably between 4 and 8. One or two CH groups in the aromatic ring systems of the formulae XIII to XVII may each be replaced by N.

$R^1$ and $R^2$, independently of one another, are identical or different and are H, F, Cl, CN or NCS. It is likewise possible for $R^1$ and/or $R^2$ to be a straight-chain or branched, optionally chiral alkyl radical or alkoxy radical having from 1 to 12 carbon atoms or an alkenyl radical or alkynyl radical having from 2 to 8 carbon atoms, where one $CH_2$ group in each of these organic radicals may also be replaced by —O—, —CO—, —O—CO—, —COO— or —CH═CH— in such a way that heteroatoms are not linked directly to one another and/or one or more H may each be replaced by halogen, preferably F.

In the case where m=0 or n=0, one $CH_2$ group in $R^1$ or $R^2$ must be replaced by one of the following groups:

a) trans-1,4-cyclohexylene, in which, in addition, one or more non-adjacent $CH_2$ groups may each be replaced by —O— or —S—, b) a radical from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl, or c) 1,4-cyclohexenylene.

The radicals a), b) and c) here may also be substituted by CN and/or halogen.

Preference is given to ring compounds of the general formula XVIII

XVIII

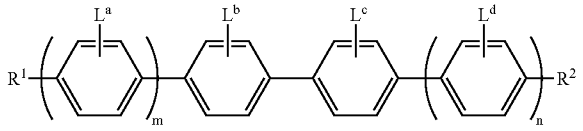

where particularly preferably m=n=1, and the radicals $R^1$ and $R^2$, independently of one another, are identical or different and are selected from the group $C_1$-$C_7$-alkyl.

Particular preference is given here to ring compounds of the following formulae XVIIIa to XVIIIg:

XVIIIa

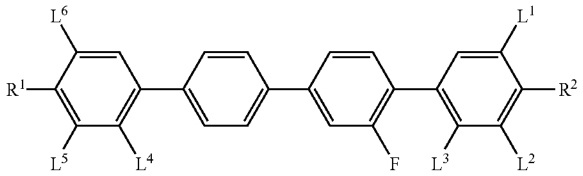

XVIIIb

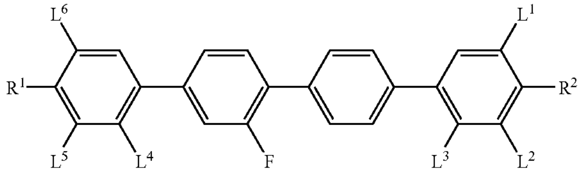

XVIIIc

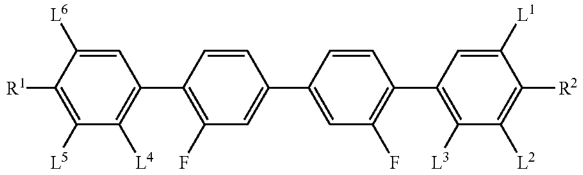

XVIIId

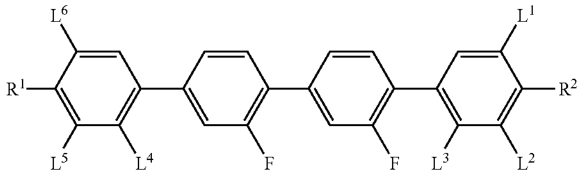

-continued

XVIIIe

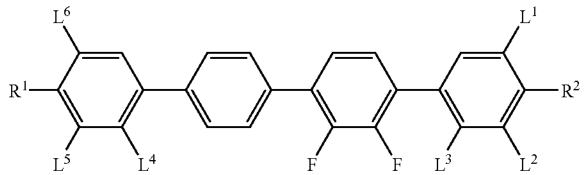

XVIIIf

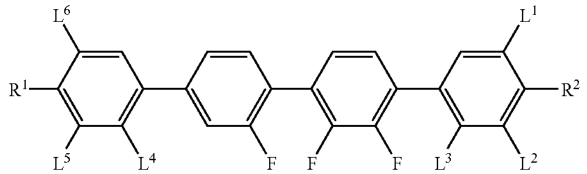

XVIIIg

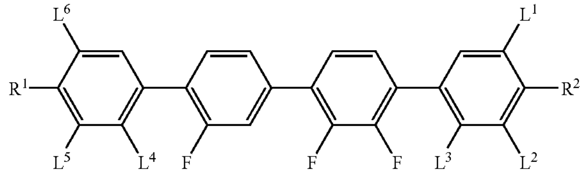

where $R^1$ and $R^2$ are as defined above in respect of formula XVIII, $L^1$, $L^2$ and $L^3$ can adopt the meanings of $L^d$, and $L^4$, $L^5$ and $L^6$ can adopt the meanings of $L^a$. Particular preference is given here to the ring compounds of the formulae XVIIIf and XVIIIg.

Boronic acids or boronic acid esters of the general formula XIX

XIX

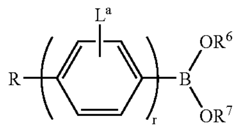

are also prepared in accordance with the invention as synthesis units.

The boronic acids or boronic acid esters preferably have a structure in accordance with the general formula XX

XX

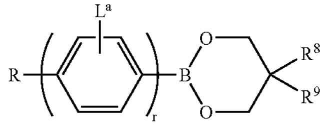

In the structures XIX and XX, r can be =m or n and can thus adopt the values 1 or 2, preferably 1. If r=m, then R=$R^1$, and if r=n, then R=$R^2$.

R can be as defined for $R^1$ and $R^2$ and is thus H, F, Cl, CN or NCS.

It is likewise possible for R to be a straight-chain or branched, optionally chiral alkyl radical or alkoxy radical having from 1 to 12 carbon atoms or an alkenyl radical or alkynyl radical having from 2 to 8 carbon atoms, where one $CH_2$ group in this organic radical may also be replaced by —O— or —COO— in such a way that heteroatoms are not linked directly to one another and/or one or more H may each be replaced by F. In addition, in the case where r=0, one $CH_2$ group in R may also be replaced by one of the following groups.

a) trans-1,4-cyclohexylene, in which, in addition, one or more non-adjacent $CH_2$ groups may each be replaced by —O— or —S—, b) a radical from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl, or c) 1,4-cyclohexenylene.

$R^6$, $R^7$, L and a here are as defined above.

$R^8$ and $R^9$, independently of one another, are identical or different and are $C_1$-$C_{12}$-alkyl or $C_{6-10}$-aryl (preferably $C_6$-aryl).

Furthermore, boronic acids or boronic acid esters of the general formula XXI

XXI

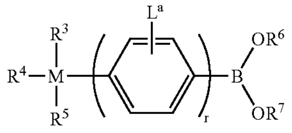

are prepared in accordance with the invention.

The boronic acids or boronic acid esters preferably have the general formula XXII

XXII

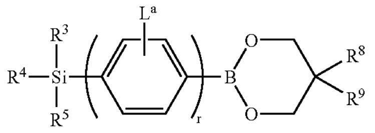

M, r, $R^3$, $R^4$, $R^5$, $R^6$, $R^7$, $R^8$, $R^9$, L and a here are as defined above.

One or two CH groups in the aromatic ring systems of the general formulae XIX, XX, XXI and XXII may likewise each be replaced by N.

The entire disclosure of all applications, patents and publications, cited above and below, and of corresponding German Application No. 10211597.4, filed Mar. 15, 2002, is hereby incorporated by reference.

The invention is described in greater detail below with reference to working examples, in which illustrative compounds according to the invention are mentioned which have been prepared by combinatorial synthesis, but without in any way being restricted thereby.

Above and below, percentages are percent by weight.

At the same time, these compounds have been characterised with reference to their phase transitions.

C denotes crystalline state, N=nematic phase, Sm=smectic phase and I=isotropic phase. The data between these symbols are the transition temperatures. All temperatures are given in degrees Celsius.

EXAMPLE 1

Preparation of the Boronic Acid (4)

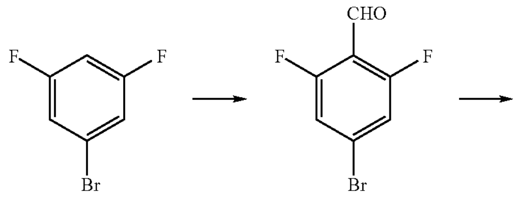

1

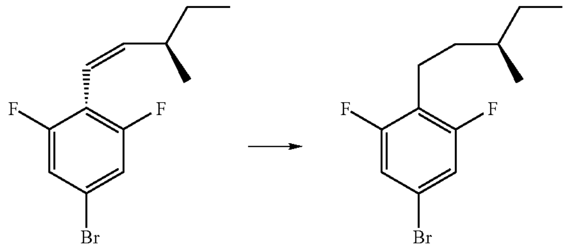

2 3

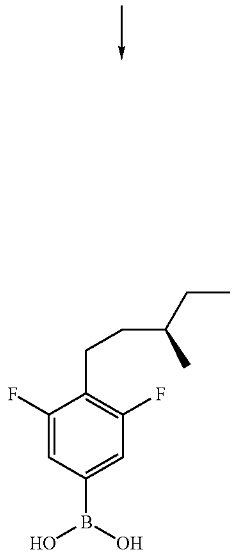

4

4-Bromo-2,6-difluorobenzaldehyde (1)

55 ml (0.11 mmol) of 2 M lithium diisopropylamide are added with stirring at −70° C. to a solution of 19.3 g (0.1 mmol) of 1-bromo-3,5-difluorobenzene in 120 ml of dried tetrahydrofuran. After 30 minutes, N-formylpiperidine is added dropwise at this temperature. The mixture is allowed to warm to 0° C. At about 0° C., the reaction mixture is poured into cold water, acidified using 10% HCl and extracted twice with methyl tert-butyl ether. The combined organic phases are washed with water, dried over $Na_2SO_4$ and filtered, and the solvent is removed under reduced pressure. The residue is filtered through $SiO_2$ (heptane/dichloromethane 1:1), (yield: 17.6 g, 78%).

5-Bromo-1,3-difluoro-2-[(R)-3-methylpent-1-enyl]benzene (2)

Phosphonium Salt Synthesis 10 g (66 mmol) of S-(+)-1-bromo-2-methylbutane and 17.4 g (66 mmol) of triphenylphosphine are dissolved in 50 ml of toluene and stirred at 110° C. for 48 hours. The mixture is allowed to warm to room temperature, and the solid is then filtered off and rinsed with toluene (6.9 g, 25%).

The phosphonium salt (6.9 g, 16.7 mmol) is suspended in 25 ml of dried tetrahydrofuran and cooled to from 0 to 5° C. At this temperature, 8.3 ml (16.7 mmol) of 2 M lithium diisopropylamide are added dropwise. After 15 minutes, a solution of 3.8 g (16.7 mmol) of 1 in 25 ml of dried tetrahydrofuran is added dropwise. The mixture is allowed to warm to room temperature and is stirred at this temperature for 1 hour. Water is subsequently added, and the mixture is acidified using 10% HCl and extracted twice with methyl tert-butyl ether. The combined organic phases are washed with water, dried over $Na_2SO_4$ and filtered, and the solvent is removed under reduced pressure. The residue is filtered through $SiO_2$ (heptane), (yield: 1.8 g, 22%).

5-Bromo-1,3-difluoro-2-[(R)-3-methylpentyl]benzene (3)

0.4 g of 5% Pt/C (dry) is added to a solution of 1.8 g (5.9 mmol) of 2 in 50 ml of heptane, and the mixture is hydrogenated at atmospheric pressure for 20 hours. The solvent is removed under reduced pressure, and the entire amount is converted into 4.

3,5-Difluoro-4-[((R)-3-methylpentyl)phenyl]phenylboronic acid (4)

3.3 ml (5.5 mmol) of 1.6 M BuLi are added dropwise at −78° C. to a solution of 1.4 g (5 mmol) of 3 in 5 ml of dry diethyl ether. After 30 minutes, 0.6 ml (5.5 mmol) of trimethyl borate is added dropwise. The mixture is allowed to warm to room temperature overnight. 5.2 ml of water, 5.2 ml of methyl tert-butyl ether and 3 ml of conc. HCl are subsequently added. The organic phase is washed with water (2×3 ml) and sat. NaCl (1×3 ml) and dried using magnesium sulfate, and the solvent is removed under reduced pressure. The residue is filtered through $SiO_2$ (heptane/dichloromethane 1:1), (yield: 0.8 g, 70%).

EXAMPLE 2

Preparation of the Biphenyl (8)

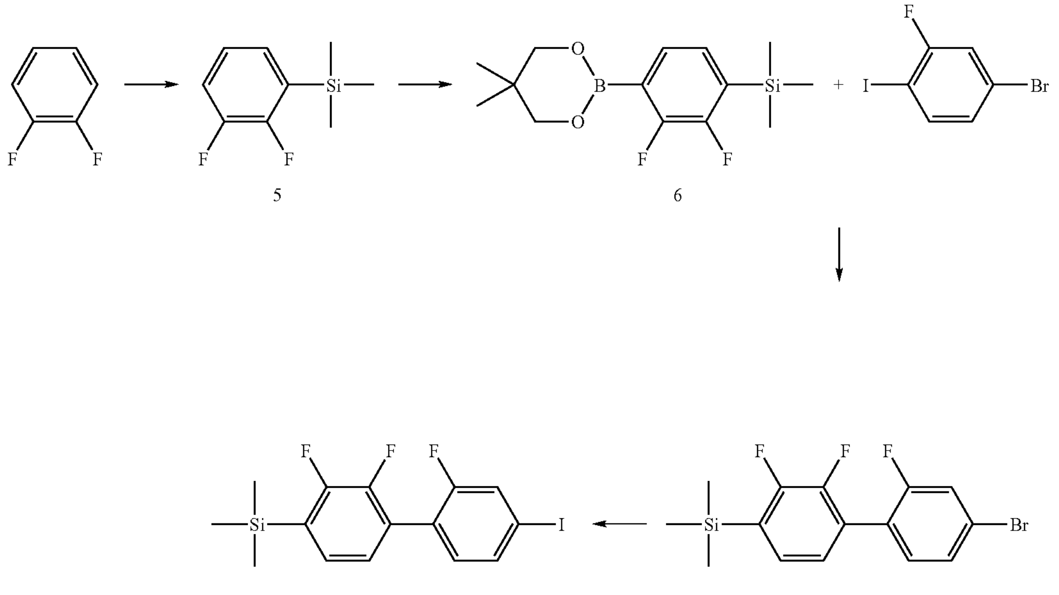

5 6 8 7

1,2-Difluoro-3-trimethylsilylbenzene (5)

625 ml (1 mol) of 1.6 M BuLi are added dropwise at −78° C. to a solution of 114 g (1 mol) of 1,2-difluorobenzene in 1 l of dry tetrahydrofuran. After 1 hour, 140 ml (120 g, 1.1 mol) of trimethylsilyl chloride are slowly added dropwise at −78° C. The mixture is allowed to warm to room temperature overnight, and then 200 ml of methyl tert-butyl ether and 200 ml of water are added. The organic phase is washed with water (2×100 ml) and sat. NaCl (1×100 ml) and dried using magnesium sulfate, and the solvent is removed under reduced pressure. 170 g (91%) of 5 distil over from the residue at from 100 to 102° C./70 mbar.

2-(2,3-Difluoro-4-trimethylsilylphenyl)-5,5-dimethyl-1,3,2-dioxaborinane (6)

625 ml (1 mol) of 1.6 M BuLi are added dropwise at −78° C. to a solution of 169 g (910 mmol) of 1,2-difluoro-3-trimethylsilylbenzene (5) in 1.4 l of dry tetrahydrofuran. After 15 minutes, 276 ml (1.2 mol) of triisopropyl borate are added dropwise. The mixture is allowed to warm to room temperature overnight. 200 ml of water, 200 ml of methyl tert-butyl ether and 100 ml of conc. HCl are subsequently added. The organic phase is washed with water (2×100 ml) and sat. NaCl (1×100 ml) and dried using magnesium sulfate, and the solvent is removed under reduced pressure. The oily residue is dissolved in 270 ml of THF, and 94 g (910 mmol) of neopentyl glycol and 455 g of magnesium sulfate are added. After the mixture has been stirred for 1 hour, the solvent is removed under reduced pressure, and petroleum ether (273 ml) is added to the oily residue. Precipitated neopentyl glycol is removed by filtration. 251 g (87%) of 6 crystallise from the filtrate at −25° C.

(4'-Bromo-2,3,2'-trifluorobiphenyl-4-yl)trimethylsilane (7)

A solution of 16.6 g (120 mmol) of $K_2CO_3$ in 50 ml of water is added to a solution of 15 g (50 mmol) of 4-bromo-2-fluoro-1-iodobenzene, 14.9 g (50 mmol) of 6 and 2.31 g (2 mmol) of $[Pd(PPh_3)_4]$ in 100 ml of dioxane, and the mixture is refluxed overnight. The organic phase is washed with water and sat. NaCl, dried over $MgSO_4$ and filtered through $SiO_2$. The solvent is removed under reduced pressure, petroleum ether is added to the oily residue, and the product is recrystallised at −25° C. (yield: 88%, m.p. 78.0° C.).

Trimethyl(2,3,2'-trifluoro-4'-iodobiphenyl-4-yl)silane (8)

30 ml (48 mmol) of 1.6 M BuLi are added dropwise at −78° C. to a solution of 15.8 g (44 mmol) of 7 in 132 ml of dry THF. After 15 minutes, 16 g (57.2 mmol) of 1,2-diiodoethane are added as solid, and the mixture is allowed to warm to room temperature over the course of 1 hour. Water and methyl tert-butyl ether are subsequently added. The organic phase is washed with water, sat. $Na_2S_2O_5$ and sat. NaCl, dried over $MgSO_4$ and filtered through $SiO_2$. The solvent is removed under reduced pressure, petroleum ether is added to the oily residue, and the product is recrystallised at −25° C. (yield: 84%, m.p. 76.0° C.).

EXAMPLE 3

Preparation of the Terphenyl (10)

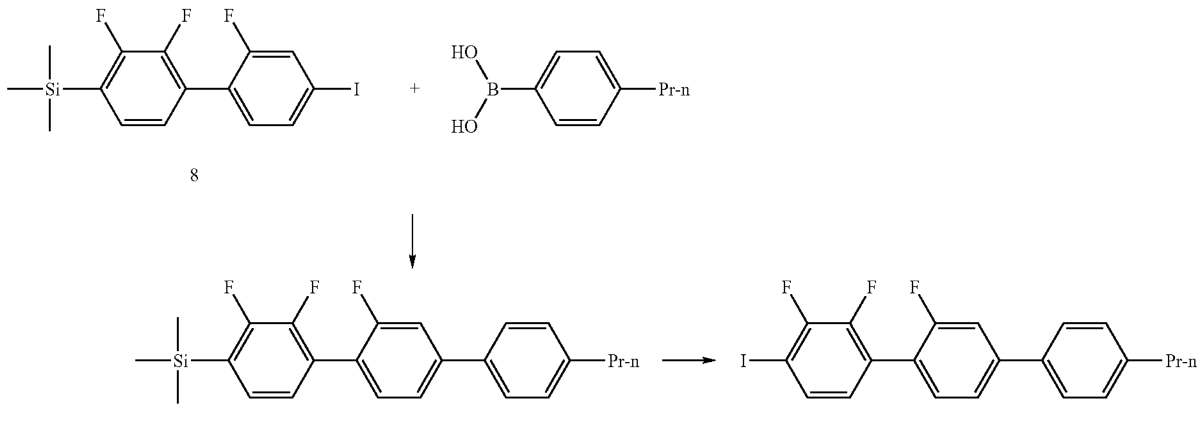

8

9 10

Trimethyl-(2,3,2'-trifluoro-4''-propyl-[1,1';4',1'']-terphenyl-4-yl)silane (9)

A solution of (2 mmol) of 8, (2.2 mmol) of 4-propylphenylboronic acid, 250 mg (2.40 mmol) of neopentyl glycol, 1.53 g (4.84 mmol) of $Ba(OH)_2 8 H_2O$, 1.35 ml (0.103 mmol, 5 mol %) of a 76 mM acetone solution of $Pd(OAc)_2$ in 20 ml of 95% i-PrOH is stirred at 80° C. for 12 hours. The solvent is subsequently removed under reduced pressure. 5 ml of 2 M HCl are added to the residue, and the mixture is extracted with dichloromethane (3×5 ml). The combined organic phases are dried over $MgSO_4$ and filtered through $SiO_2$. The solvent is removed under reduced pressure, and the residue is converted into 10 (yield: 89%).

2,3,2'-Trifluoro-4-iodo-4''-propyl-[1,1';4',1'']-terphenyl (10)

The total amount of the terphenyl 9 is dissolved in 4 ml of absolute acetonitrile and reacted with 1.2 ml (6 mmol) of a 5 M solution of ICl in acetonitrile, and the mixture is stirred at room temperature for 1 hour. The residue is crystallised at −20° C. for 2 hours. The supernatant solution is subsequently sucked off, and the product which remains is washed with 2 M $Na_2S_2O_5$ (10 ml) and water (10 ml) and dried in an oil-pump vacuum (yield: 54%).

EXAMPLE 4

Preparation of the Quaterphenyl (11)

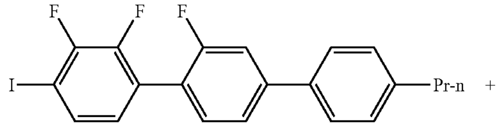

10

-continued

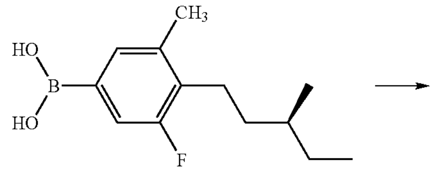

4

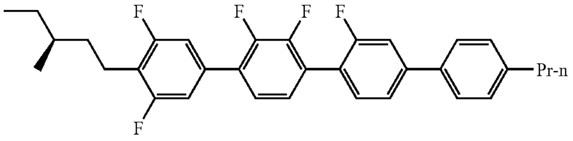

11

3,5,2',3',2''-Pentafluoro-4'''-methyl-4-((S)-3-methylpentyl)-[1,4'; 1', 1'';4'', 1''']-quaterphenyl (11)

A solution of (0.1 mmol) of 10, (0.12 mmol) of 4, 14 mg (0.13 mmol) of neopentyl glycol, 95 mg (0.3 mmol) of $Ba(OH)_2$ $.8H_2O$, 80 μl (6.08 mmol, 5 mol %) of a 76 mM acetone solution of $Pd(OAc)_2$ in 2 ml of 95% i-PrOH is stirred at 80° C. for 12 hours. The solvent is subsequently removed under reduced pressure. 2 ml of 2 M HCl are added to the residue, and the mixture is extracted with dichloromethane (3×2 ml). The combined organic phases are dried over $MgSO_4$ and filtered through $SiO_2$. The solvent is removed under reduced pressure, and the residue is purified by recrystallisation twice from nonane (yield: 60%).

1% by weight of the quaterphenyl (11) is added to a commercially available nematic base mixture MLC-6260 from Merck KGaA, Darmstadt, and the twisting power HTP of the composition is determined by the Grandjean-Cano method at 20° C. The composition has an HTP of −1.9.

EXAMPLE 5

Preparation of the Quaterphenyl (13)

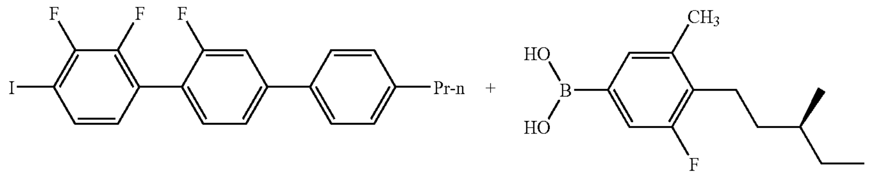

10 12

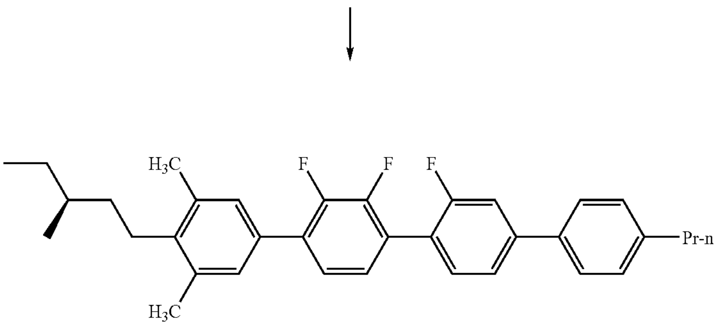

13

2',3',2"-Trifluoro-3,5-dimethyl-4-((S)-3-methylpentyl)-4'"-propyl-[1,4';1', 1";4",1'"]-quaterphenyl (13)

A solution of (0.1 mmol) of 10, (0.12 mmol) of 12, 14 mg (0.13 mmol) of neopentyl glycol, 95 mg (0.3 mmol) of $Ba(OH)_2.8H_2O$, 80 μl (6.08 mmol, 5 mol %) of a 76 mM acetone solution of $Pd(OAc)_2$ in 2 ml of 95% i-PrOH is stirred at 80° C. for 12 hours. The solvent is subsequently removed under reduced pressure. 2 ml of 2 M HCl are added to the residue, and the mixture is extracted with dichloromethane (3×2 ml). The combined organic phases are dried over $MgSO_4$ and filtered through $SiO_2$. The solvent is removed under reduced pressure, and the residue is purified by recrystallisation twice from nonane (yield: 65%).

1% by weight of the quaterphenyl (13) is added to a commercially available nematic base mixture MLC-6260 from Merck KGaA, Darmstadt, and the twisting power HTP of the composition is determined by the Grandjean-Cano method at 20° C. The composition has an HTP of −1.5.

1% by weight of the quaterphenyl (13) is added to a commercially available nematic base mixture MJ-001667 from Merck KGaA, Darmstadt, and the twisting power HTP of the composition is determined by the Grandjean-Cano method at 20° C. The composition has an HTP of −1.9.

EXAMPLE 6

Preparation of the Quaterphenyl (15)

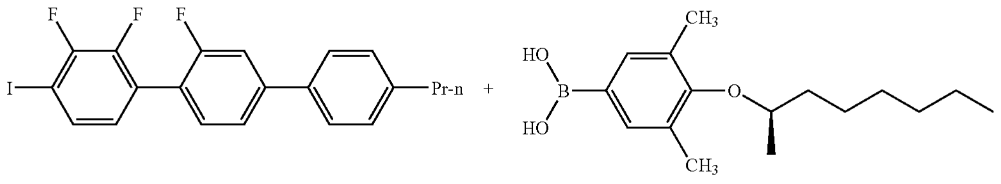

10 14

-continued

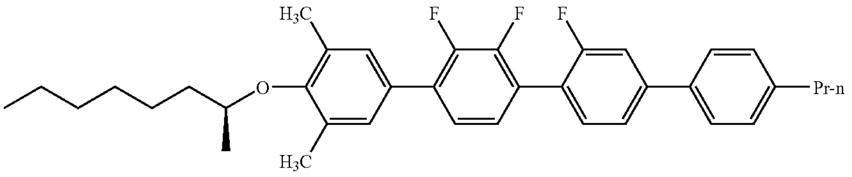

15

2',3',2"-Trifluoro-3,5-dimethyl-4-((S)-1-methylheptyloxy)-4'"-propyl-[1,4';1',1";4",1'"]-quaterphenyl (15)

A solution of (0.1 mmol) of 10, (0.12 mmol) of 14, 14 mg (0.13 mmol) of neopentyl glycol, 95 mg (0.3 mmol) of $Ba(OH)_2.8H_2O$, 80 μl (6.08 mmol, 5 mol %) of a 76 mM acetone solution of $Pd(OAc)_2$ in 2 ml of 95% i-PrOH is stirred at 80° C. for 12 hours. The solvent is subsequently removed under reduced pressure. 2 ml of 2 M HCl are added to the residue, and the mixture is extracted with dichloromethane (3×2 ml). The combined organic phases are dried over $MgSO_4$ and filtered through $SiO_2$. The solvent is removed under reduced pressure, and the residue is purified by recrystallisation twice from nonane (yield: 68%).

1% by weight of the quaterphenyl (15) is added to a commercially available nematic base mixture MLC-6260 from Merck KGaA, Darmstadt, and the twisting power HTP of the composition is determined by the Grandjean-Cano method at 20° C. The composition has an HTP of −12.1.

1% by weight of the quaterphenyl (15) is added to a commercially available nematic base mixture MJ-001667 from Merck KGaA, Darmstadt, and the twisting power HTP of the composition is determined by the Grandjean-Cano method at 20° C. The composition has an HTP of −19.5.

The compounds of the following examples are prepared analogously to Examples 1 to 6 and reaction schemes 1 to 4 using the corresponding starting compounds:

EXAMPLES 7 TO 21

TABLE 1

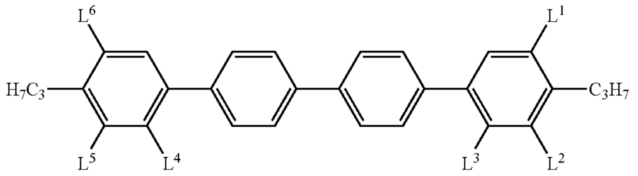

| Example | $L^1$ | $L^2$ | $L^3$ | $L^4$ | $L^5$ | $L^6$ | Phase transitions [° C.] |
|---|---|---|---|---|---|---|---|
| 7 | H | H | H | H | H | H | |
| 8 | H | F | H | H | H | H | C 264 SmE 276 SmA 351 N 355 I |
| 9 | H | H | F | H | H | H | C 190 Sm? 210 SmC 237 SmA 250 N 335.2 I |
| 10 | F | F | H | H | H | H | C 158 SmE 243 SmA 326 I |
| 11 | H | F | F | H | H | H | C 197 SmC 218 SmA 300 N 332.5 I |
| 12 | H | F | H | F | H | H | C 191 SmC 202 SmA 263 N 304.7 I |
| 13 | H | F | H | H | F | H | C 239 SmA 322 I |
| 14 | H | H | F | F | H | H | C 174 N 297.5 I |
| 15 | F | F | H | F | H | H | C 145 SmA 270 N 274 I |
| 16 | F | F | H | H | F | H | C 190 SmA 292 I |
| 17 | H | F | F | F | H | H | C 183 N 290.8 I |
| 18 | H | F | F | H | F | H | C 177 SmA 282 N 300.1 I |
| 19 | F | F | H | F | F | H | C 154 SmA 265 N 269 I |
| 20 | F | F | H | H | F | F | C 203 SmA 249 N 250.6 I |
| 21 | H | F | F | F | F | H | C 178 SmC 206 SmA 219 N 284.4 I |

EXAMPLES 22 TO 46

TABLE 2

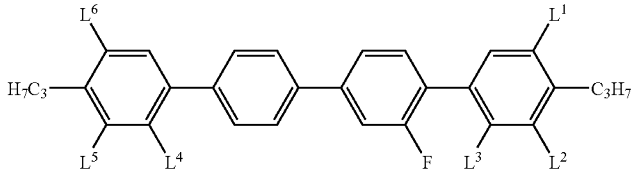

| Example | $L^1$ | $L^2$ | $L^3$ | $L^4$ | $L^5$ | $L^6$ | Phase transitions [° C.] |
|---|---|---|---|---|---|---|---|
| 22 | H | H | H | H | H | H | C 146 Sm? 184 SmC 198 SmA 283 N 336.8 I |
| 23 | H | F | H | H | H | H | C 161 SmC 165 SmA 293 N 313.7 I |
| 24 | H | H | F | H | H | H | C 128 SmC 162 SmA 186 N 297.6 I |
| 25 | H | H | H | F | H | H | C 127 N 297.8 I |
| 26 | H | H | H | H | F | H | C 152 SmA 227 N 307.0 I |
| 27 | F | F | H | H | H | H | C 105 Sm? 152 SmA 284 N 287.2 I |
| 28 | H | F | F | H | H | H | C 130 SmC (119) SmA 232 N 295.5 I |
| 29 | H | H | H | F | F | H | |
| 30 | H | H | H | H | F | F | C 152 SmA 268 N 274 I |
| 31 | H | F | H | H | F | H | C 139 SmA 266 N 283.9 I |
| 32 | H | F | H | F | H | H | C 106 SmC 106 SmA 198 N 272.1 I |
| 33 | H | H | F | H | F | H | C 97 SmC 144 SmA 153 N 264.5 I |
| 34 | H | H | F | F | H | H | C 120 N 257.7 I |
| 35 | F | F | H | F | H | H | C 95 SmA 226 N 245.0 I |
| 36 | F | F | H | H | F | H | C 118 SmA 243 N 255.7 I |
| 37 | H | F | F | F | H | H | C 129 N 251.0 I |
| 38 | H | F | F | H | F | H | C 112 SmC (110) SmA 211 N 260.1 I |
| 39 | H | F | H | H | F | F | C 129 SmA 242 N 251.0 I |
| 40 | H | H | F | H | F | F | C 122 SmA 197 N 231.5 I |
| 41 | H | F | H | F | F | H | |
| 42 | H | H | F | F | F | H | |
| 43 | F | F | H | H | F | F | C 158 SmA 206 N 223.7 I |
| 44 | F | F | H | F | F | H | |
| 45 | H | F | F | H | F | F | C 124 SmA 208 N 228.4 I |
| 46 | H | F | F | F | F | H | |

EXAMPLES 47 TO 71

TABLE 3

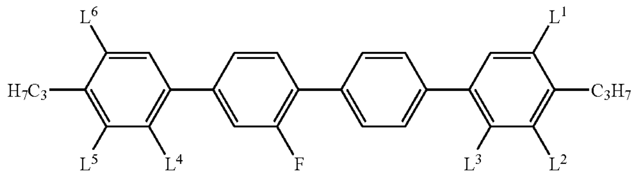

| Example | $L^1$ | $L^2$ | $L^3$ | $L^4$ | $L^5$ | $L^6$ | Phase transitions [° C.] |
|---|---|---|---|---|---|---|---|
| 47 | H | H | H | H | H | H | C 186 Sm? 188 N 330.8 I |
| 48 | H | F | H | H | H | H | C 144 SmC (141) SmA 251 N 297.9 I |
| 49 | H | H | F | H | H | H | C 118 N 295.1 I |
| 50 | H | H | H | F | H | H | C 112 N 299.7 I |
| 51 | H | H | H | H | F | H | C 148 SmA 246 N 299.4 I |
| 52 | F | F | H | H | H | H | C 150 SmA 260 N 267.9 I |
| 53 | H | F | F | H | H | H | C 133 SmA 152 N 287.6 I |
| 54 | H | H | H | F | F | H | C 124 SmA 147 N 289.1 I |
| 55 | H | H | H | H | F | F | C 136 SmA 260 N 264.0 I |

TABLE 3-continued

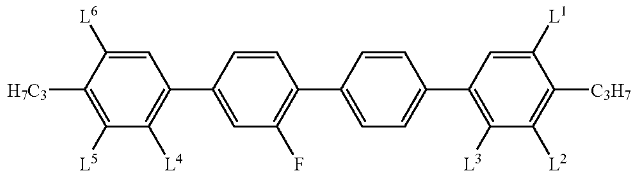

| Example | $L^1$ | $L^2$ | $L^3$ | $L^4$ | $L^5$ | $L^6$ | Phase transitions [° C.] |
|---|---|---|---|---|---|---|---|
| 56 | H | F | H | H | F | H | C 125 SmA 249 N 271.8 I |
| 57 | H | F | H | F | H | H | C 121 N 264.5 I |
| 58 | H | H | F | H | F | H | C 128 N 262.6 I |
| 59 | H | H | F | F | H | H | C 131 N 267.1 I |
| 60 | F | F | H | F | H | H | C 123 SmA 182 N 225.9 I |
| 61 | F | F | H | H | F | H | C 152 SmA 240 N 242.0 I |
| 62 | H | F | F | F | H | H | C 146 N 256.1 I |
| 63 | H | F | F | H | F | H | C 136 SmA 187 N 256.6 I |
| 64 | H | F | H | H | F | F | C 151 SmA 243 N 243.0 I |
| 65 | H | H | F | H | F | F | C 141 SmA 181 N 226.3 I |
| 66 | H | F | H | F | F | H | C 129 SmC 174 SmA 186 N 257.7 I |
| 67 | H | H | F | F | F | H | C 146 N 254.8 I |
| 68 | F | F | H | H | F | F | C 191 SmA 219 I |
| 69 | F | F | H | F | F | H | C 133 SmA 206 N 225.1 I |
| 70 | H | F | F | H | F | F | C 145 SmA 208 N 224.5 I |
| 71 | H | F | F | F | F | H | C 159 N 245.4 I |

EXAMPLES 72 TO 86

TABLE 4

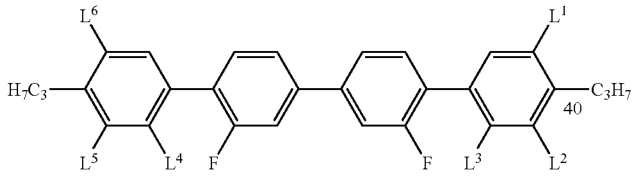

| Example | $L^1$ | $L^2$ | $L^3$ | $L^4$ | $L^5$ | $L^6$ | Phase transitions |
|---|---|---|---|---|---|---|---|
| 72 | H | H | H | H | H | H | C 131 SmC (113) SmA 186 N 293.6 I |
| 73 | H | F | H | H | H | H | C 96 SmA 223 N 270.3 I |
| 74 | H | H | F | H | H | H | C 129 N 256.5 I |
| 75 | F | F | H | H | H | H | C 117 SmA 226 N 244.4 I |
| 76 | H | F | F | H | H | H | C 126 N 254.4 I |
| 77 | H | F | H | F | H | H | C 134 N 234.6 I |
| 78 | H | F | H | H | F | H | C 120 SmA 217 N 250.0 I |
| 79 | H | H | F | F | H | H | C 156 N 222.6 I |
| 80 | F | F | H | F | H | H | C 145 SmA 167 N 209.7 I |
| 81 | F | F | H | H | F | H | C 150 SmA 202 N 224.7 I |
| 82 | H | F | F | F | H | H | C 155 N 214.8 I |
| 83 | H | F | F | H | F | H | C 141 SmA 160 N 242.0 I |
| 84 | F | F | H | F | F | H | C 159 SmA 172 N 203.8 I |
| 85 | F | F | H | H | F | F | C 190 N 205.0 I |
| 86 | H | F | F | F | F | H | C 162 N 214.8 I |

EXAMPLES 87 TO 111

TABLE 5

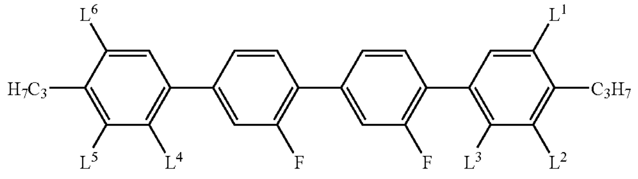

| Example | $L^1$ | $L^2$ | $L^3$ | $L^4$ | $L^5$ | $L^6$ | Phase transitions [° C.] |
|---|---|---|---|---|---|---|---|
| 87 | H | H | H | H | H | H | C 118 N 296.0 I |
| 88 | H | F | H | H | H | H | C 98 SmA 197 N 269.1 I |
| 89 | H | H | F | H | H | H | C 128 N 262.1 I |
| 90 | H | H | H | F | H | H | C 134 N 265.1 I |
| 91 | H | H | H | H | F | H | C 111 SmA 167 N 263.8 I |
| 92 | F | F | H | H | H | H | C 109 SmA 222 N 238.6 I |
| 93 | H | F | F | H | H | H | C 143 N 249.2 I |
| 94 | H | H | H | F | F | H | C 139 N 253.0 I |
| 95 | H | H | H | H | F | F | C 129 SmA 205 N 229.7 I |
| 96 | H | F | H | H | F | H | C 120 SmA 205 N 244.1 I |
| 97 | H | F | H | F | H | H | C 139 N 238.5 I |
| 98 | H | H | F | H | F | H | C 136 N 232.1 I |
| 99 | H | H | F | F | H | H | C 157 N 234.3 I |
| 100 | F | F | H | F | H | H | C 149 SmA 160 N 207.8 I |
| 101 | F | F | H | H | F | H | C 128 SmA 204 N 220.1 I |
| 102 | H | F | F | F | H | H | C 162 N 222.2 I |
| 103 | H | F | F | H | F | H | C 151 N 224.5 I |
| 104 | H | F | H | H | F | F | C 134 SmA 204 N 217.1 I |
| 105 | H | H | F | H | F | F | C 161 N 200.7 I |
| 106 | H | F | H | F | F | H | C 152 SmA 148 N 229.0 I |
| 107 | H | H | F | F | F | H | C 164 N 220.4 I |
| 108 | F | F | H | H | F | F | C 170 SmA 190 N 199.2 I |
| 109 | F | F | H | F | F | H | C 157 SmA 177 N 203.4 I |
| 110 | H | F | F | H | F | F | C 169 SmA (158) N 196.9 I |
| 111 | H | F | F | F | F | H | C 173 N 212.9 I |

EXAMPLES 112 TO 136

TABLE 6

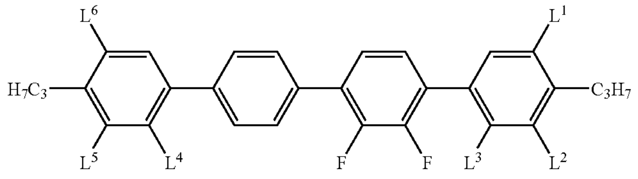

| Example | $L^1$ | $L^2$ | $L^3$ | $L^4$ | $L^5$ | $L^6$ | Phase transitions [° C.] |
|---|---|---|---|---|---|---|---|
| 112 | H | H | H | H | H | H | C 131 N 318.0 I |
| 113 | H | F | H | H | H | H | C 97 SmA 227 N 286.1 I |
| 114 | H | H | F | H | H | H | C 131 N 281.2 I |
| 115 | H | H | H | F | H | H | C 136 N 274.2 I |
| 116 | H | H | H | H | F | H | C 109 SmA 216 N 280.9 I |
| 117 | F | F | H | H | H | H | C 94 SmA 251 N 261.8 I |
| 118 | H | F | F | H | H | H | C 130 SmA (113) N 271.8 I |
| 119 | H | H | H | F | F | H | C 139 N 276.8 I |
| 120 | H | H | H | H | F | F | C 146 SmA 234 N 252.5 I |
| 121 | H | F | H | H | F | H | C 114 SmA 233 N 262.8 I |
| 122 | H | F | H | F | H | H | C 131 N 233.4 I |
| 123 | H | H | F | H | F | H | C 130 N 245.2 I |
| 124 | H | H | F | F | H | H | C 160 N 241.8 I |
| 125 | F | F | H | F | H | H | C 148 SmA 177 N 214.6 I |
| 126 | F | F | H | H | F | H | C 113 SmA 225 N 235.4 I |
| 127 | H | F | F | F | H | H | C 149 N 235.7 I |
| 128 | H | F | F | H | F | H | C 144 N 242.3 I |
| 129 | H | F | H | H | F | F | C 139 SmA 228 N 234.8 I |

TABLE 6-continued

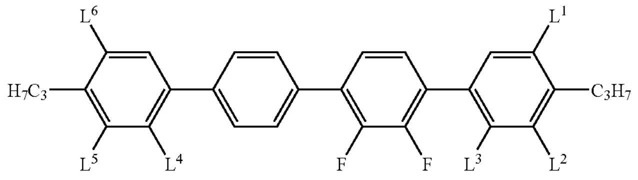

| Example | $L^1$ | $L^2$ | $L^3$ | $L^4$ | $L^5$ | $L^6$ | Phase transitions [° C.] |
|---|---|---|---|---|---|---|---|
| 130 | H | H | F | H | F | F | C 152 SmA 176 N 212.6 I |
| 131 | H | F | H | F | F | H | C 151 SmA 176 N 250.7 I |
| 132 | H | H | F | F | F | H | C 162 N 240.1 I |
| 133 | F | F | H | H | F | F | C 152 SmA 208 N 212.6 I |
| 134 | F | F | H | F | F | H | C 151 SmA 204 N 223.2 I |
| 135 | H | F | F | H | F | F | C 156 SmA 179 N 210.7 I |
| 136 | H | F | F | F | F | H | C 172 N 235.6 I |

EXAMPLES 137 TO 151

TABLE 7

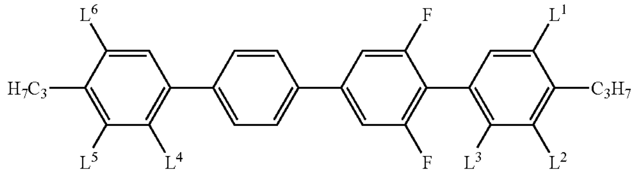

| Example | $L^1$ | $L^2$ | $L^3$ | $L^4$ | $L^5$ | $L^6$ | Phase transitions [° C.] |
|---|---|---|---|---|---|---|---|
| 137 | H | H | H | H | H | H | |
| 138 | H | F | H | H | H | H | C 148 SmA 236 N 274.5 I |
| 139 | H | H | H | F | H | H | C 132 N 257.8 I |
| 140 | H | H | H | H | F | H | C 146 SmA 214 N 267.3 I |
| 141 | F | F | H | H | H | H | |
| 142 | H | H | H | F | F | H | C 138 N 251.2 I |
| 143 | H | H | H | H | F | F | C 186 SmA 217 N 236.3 I |
| 144 | H | F | H | H | F | H | |
| 145 | H | F | H | F | H | H | C 133 SmA 154 N 238.9 I |
| 146 | F | F | H | F | H | H | |
| 147 | F | F | H | H | F | H | |
| 148 | H | F | H | H | F | F | C 154 SmA 198 N 219.5 I |
| 149 | H | F | H | F | F | H | C 141 SmA 173 N 229.5 I |
| 150 | F | F | H | H | F | F | |
| 151 | F | F | H | F | F | H | |

EXAMPLES 152 TO 176

TABLE 8

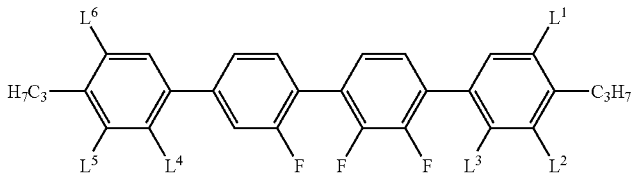

| Example | $L^1$ | $L^2$ | $L^3$ | $L^4$ | $L^5$ | $L^6$ | Phase transitions [° C.] |
|---|---|---|---|---|---|---|---|
| 152 | H | H | H | H | H | H | C 150 Sm? (137) N 267.7 I |
| 153 | H | F | H | H | H | H | C 153 N 240.5 I |
| 154 | H | H | F | H | H | H | C 172 N 240.5 I |

TABLE 8-continued

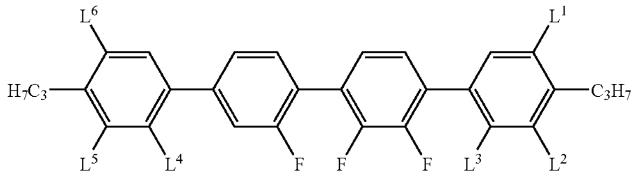

| Example | $L^1$ | $L^2$ | $L^3$ | $L^4$ | $L^5$ | $L^6$ | Phase transitions [° C.] |
|---|---|---|---|---|---|---|---|
| 155 | H | H | H | F | H | H | C 176 N 243.2 I |
| 156 | H | H | H | H | F | H | C 157 N 214.9 I |
| 157 | F | F | H | H | H | H | C 161 SmA 166 N 207.1 I |
| 158 | H | F | F | H | H | H | C 178 N 232.5 I |
| 159 | H | H | H | F | F | H | C 173 N 203.1 I |
| 160 | H | H | H | H | F | F | C 160 N 203.5 I |
| 161 | H | F | H | H | F | H | C 151 N 238.6 I |
| 162 | H | F | H | F | H | H | C 174 N 211.1 I |
| 163 | H | H | F | H | F | H | C 172 N 210.1 I |
| 164 | H | H | F | F | H | H | C 196 N 211.0 I |
| 165 | F | F | H | F | H | H | C 185 N (181.3) I |
| 166 | F | F | H | H | F | H | C 166 SmA 176 N 193.3 I |
| 167 | H | F | F | F | H | H | C 193 N 206.0 I |
| 168 | H | F | F | H | F | H | C 176 N 198.8 I |
| 169 | H | F | H | H | F | F | C 163 SmA 174 N 193.3 I |
| 170 | H | H | F | H | F | F | C 182 N (178.5) I |
| 171 | H | F | H | F | F | H | C 183 N 208.1 I |
| 172 | H | H | F | F | F | H | C 193 N 206.1 I |
| 173 | F | F | H | H | F | F | C 183 SmA (181) N (182.5) I |
| 174 | F | F | H | F | F | H | C 188 N (183.0) I |
| 175 | H | F | F | H | F | F | C 183 N (173.1) I |
| 176 | H | F | F | F | F | H | |

EXAMPLES 177 TO 201

TABLE 9

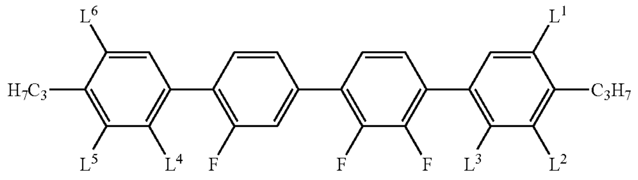

| Example | $L^1$ | $L^2$ | $L^3$ | $L^4$ | $L^5$ | $L^6$ | Phase transitions [° C.] |
|---|---|---|---|---|---|---|---|
| 177 | H | H | H | H | H | H | C 144 N 281.2 I |
| 178 | H | F | H | H | H | H | C 143 SmA 160 N 256.2 I |
| 179 | H | H | F | H | H | H | C 164 N 247.3 I |
| 180 | H | H | H | F | H | H | C 165 N 249.3 I |
| 181 | H | H | H | H | F | H | C 142 SmA 174 N 256.2 I |
| 182 | F | F | H | H | H | H | C 139 SmA 200 N 226.7 I |
| 183 | H | F | F | H | H | H | C 162 N 241.7 I |
| 184 | H | H | H | F | F | H | C 169 N 241.2 I |
| 185 | H | H | H | H | F | F | C 144 SmA 207 N 226.8 I |
| 186 | H | F | H | H | F | H | C 150 SmA 194 N 234.7 I |
| 187 | H | F | H | F | H | H | C 161 N 222.2 I |
| 188 | H | H | F | H | F | H | C 162 N 222.2 I |
| 189 | H | H | F | F | H | H | C 182 N 216.3 I |
| 190 | F | F | H | F | H | H | C 173 N 192.8 I |
| 191 | F | F | H | H | F | H | C 154 SmA 193 N 209.0 I |
| 192 | H | F | F | F | H | H | C 178 N 209.1 I |
| 193 | H | F | F | H | F | H | C 169 N 216.8 I |
| 194 | H | F | H | H | F | F | C 157 SmA 197 N 212.6 I |
| 195 | H | H | F | H | F | F | C 169 N 193.7 I |
| 196 | H | F | H | F | F | H | C 172 N 217.3 I |
| 197 | H | H | F | F | F | H | C 179 N 206.1 I |
| 198 | F | F | H | H | F | F | C 179 SmA 181 N 192.8 I |
| 199 | F | F | H | F | F | H | C 175 N 190.5 I |

TABLE 9-continued

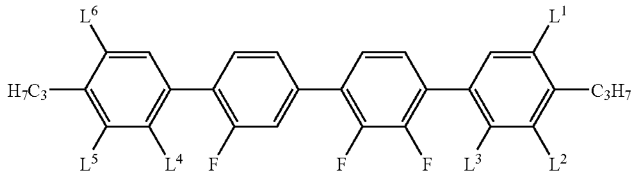

| Example | $L^1$ | $L^2$ | $L^3$ | $L^4$ | $L^5$ | $L^6$ | Phase transitions [° C.] |
|---|---|---|---|---|---|---|---|
| 200 | H | F | F | H | F | F | C 176 N 190.4 I |
| 201 | H | F | F | F | F | H | C 188 N 201.9 I |

EXAMPLES 202 TO 216

TABLE 10

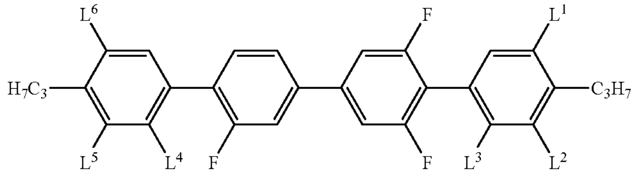

| Example | $L^1$ | $L^2$ | $L^3$ | $L^4$ | $L^5$ | $L^6$ | Phase transitions [° C.] |
|---|---|---|---|---|---|---|---|
| 202 | H | H | H | H | H | H | |
| 203 | H | F | H | H | H | H | |
| 204 | H | H | H | F | H | H | |
| 205 | H | H | H | H | F | H | |
| 206 | F | F | H | H | H | H | |
| 207 | H | H | H | F | F | H | |
| 208 | H | H | H | H | F | F | |
| 209 | H | F | H | H | F | H | |
| 210 | H | F | H | F | H | H | |
| 211 | F | F | H | F | H | H | |
| 212 | F | F | H | H | F | H | |
| 213 | H | F | H | H | F | F | |
| 214 | H | F | H | F | F | H | |
| 215 | F | F | H | H | F | F | |
| 216 | F | F | H | F | F | H | |

EXAMPLES 217 TO 231

TABLE 11

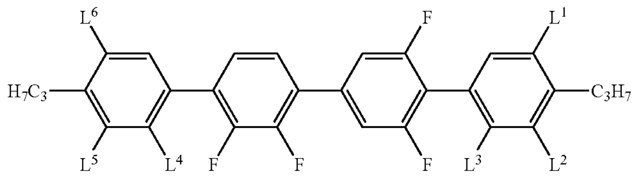

| Example | $L^1$ | $L^2$ | $L^3$ | $L^4$ | $L^5$ | $L^6$ | Phase transitions [° C.] |
|---|---|---|---|---|---|---|---|
| 217 | H | H | H | H | H | H | C 172 N 249.0 I |
| 218 | H | F | H | H | H | H | C 168 N 228.9 I |
| 219 | H | H | H | F | H | H | C 185 N 216.2 I |
| 220 | H | H | H | H | F | H | C 169 N 224.0 I |
| 221 | F | F | H | H | H | H | — |
| 222 | H | H | H | F | F | H | C 185 N 210.6 I |
| 223 | H | H | H | H | F | F | C 174 SmA (165) N 199.1 I |
| 224 | H | F | H | H | F | H | C 172 SmA (166) N 210.8 I |

TABLE 11-continued

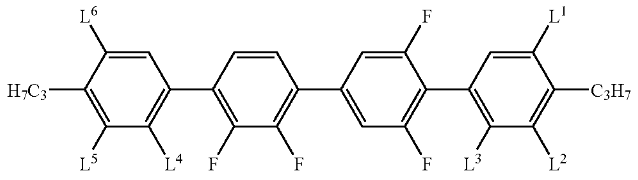

| Example | $L^1$ | $L^2$ | $L^3$ | $L^4$ | $L^5$ | $L^6$ | Phase transitions [° C.] |
|---|---|---|---|---|---|---|---|
| 225 | H | F | H | F | H | H | C 182 N 195.5 I |
| 226 | F | F | H | F | H | H | C 186 I |
| 227 | F | F | H | H | F | H | C 182 SmA 194 N 240.6 I |
| 228 | H | F | H | H | F | F | C 181 SmA ? N 190.3 I |
| 229 | H | F | H | F | F | H | C 186 N 192.0 I |
| 230 | F | F | H | H | F | F | C 194 I |
| 231 | F | F | H | F | F | H | C 192 I |

EXAMPLES 232 TO 247

TABLE 12

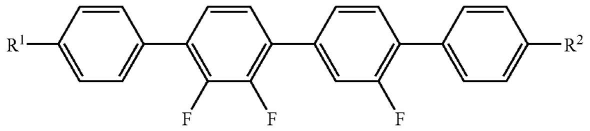

| Example | $R^1$ | $R^2$ | Phase transitions [° C.] |
|---|---|---|---|
| 232 | $C_3H_7$ | $C_3H_7$ | |
| 233 | $C_3H_7$ | $C_4H_9$ | |
| 234 | $C_3H_7$ | $C_5H_{11}$ | |
| 235 | $C_3H_7$ | $C_6H_{13}$ | |
| 236 | $C_4H_9$ | $C_3H_7$ | C 127 N 263.6 I |
| 237 | $C_4H_9$ | $C_4H_9$ | C 124 N 251.7 I |
| 238 | $C_4H_9$ | $C_5H_{11}$ | |
| 239 | $C_4H_9$ | $C_6H_{13}$ | |
| 240 | $C_5H_{11}$ | $C_3H_7$ | |
| 241 | $C_5H_{11}$ | $C_4H_9$ | |
| 242 | $C_5H_{11}$ | $C_5H_{11}$ | |
| 243 | $C_5H_{11}$ | $C_6H_{13}$ | |
| 244 | $C_6H_{13}$ | $C_3H_7$ | |
| 245 | $C_6H_{13}$ | $C_4H_9$ | |
| 246 | $C_6H_{13}$ | $C_5H_{11}$ | |
| 247 | $C_6H_{13}$ | $C_6H_{13}$ | |

EXAMPLES 248 TO 272

TABLE 13

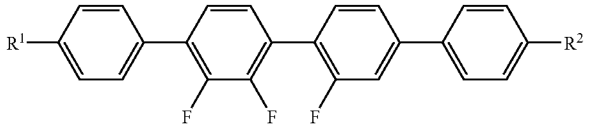

| Example | $R^1$ | $R^2$ | Phase transitions [° C.] |
|---|---|---|---|
| 248 | $C_3H_7$ | $C_3H_7$ | |
| 249 | $C_3H_7$ | t-$C_4H_9$ | |
| 250 | $C_3H_7$ | $C_5H_{11}$ | C 99 N 250.6 I |
| 251 | $C_3H_7$ | $C_6H_{13}$ | |
| 252 | $C_3H_7$ | $C_{10}H_{21}$ | C 93 N 207.9 I |
| 253 | t-$C_4H_9$ | $C_3H_7$ | |
| 254 | t-$C_4H_9$ | t-$C_4H_9$ | |

TABLE 13-continued

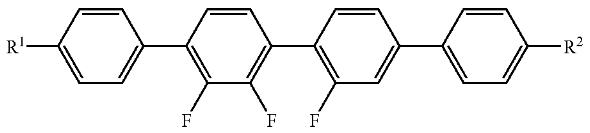

| Example | $R^1$ | $R^2$ | Phase transitions [° C.] |
|---|---|---|---|
| 255 | t-$C_4H_9$ | $C_5H_{11}$ | C 133 N 140.8 I |
| 256 | t-$C_4H_9$ | $C_6H_{13}$ | |
| 257 | t-$C_4H_9$ | $C_{10}H_{21}$ | C 115 N 119.3 I |
| 258 | $C_5H_{11}$ | $C_3H_7$ | C 103 N 252.5 I |
| 259 | $C_5H_{11}$ | t-$C_4H_9$ | C 134 N 144.3 I |
| 260 | $C_5H_{11}$ | $C_5H_{11}$ | C 106 N 234.4 I |
| 261 | $C_5H_{11}$ | $C_6H_{13}$ | |
| 262 | $C_5H_{11}$ | $C_{10}H_{21}$ | C 85 Sm?; N 198.7 I |
| 263 | $C_6H_{13}$ | $C_3H_7$ | |
| 264 | $C_6H_{13}$ | t-$C_4H_9$ | |
| 265 | $C_6H_{13}$ | $C_5H_{11}$ | |
| 266 | $C_6H_{13}$ | $C_6H_{13}$ | |
| 267 | $C_6H_{13}$ | $C_{10}H_{21}$ | |
| 268 | $C_{10}H_{21}$ | $C_3H_7$ | C 103 SmC 114 N 205.1 I |
| 269 | $C_{10}H_{21}$ | t-$C_4H_9$ | C 101 SmC 123 N 127.5 I |
| 270 | $C_{10}H_{21}$ | $C_5H_{11}$ | C 102 SmC 135 N 197.5 I |
| 271 | $C_{10}H_{21}$ | $C_6H_{13}$ | |
| 272 | $C_{10}H_{21}$ | $C_{10}H_{21}$ | C 104 SmC 158 N 177.3 I |

EXAMPLE 273

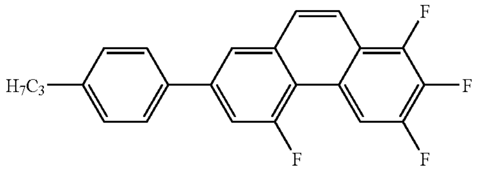

Phase transitions [° C.]: C 108 SmA 109 N 133.1 I

EXAMPLE 274

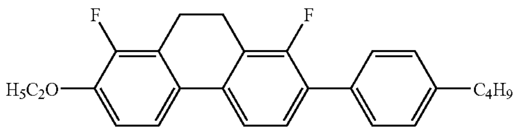

Phase transitions [° C.]: C 113 SmA 141 N 204.0 I

EXAMPLE 275

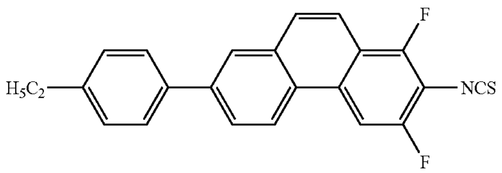

Phase transitions [° C.]: C 127 N

EXAMPLE 276

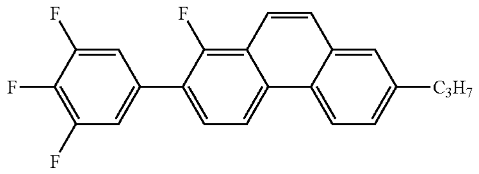

Phase transitions [° C.]: C 114 SmC 136 I

EXAMPLE 277

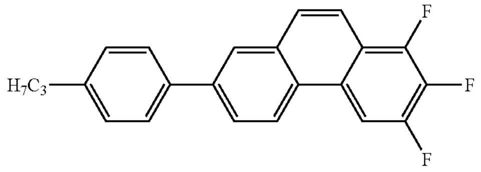

Phase transitions [° C.]: C 131 SmA 143 I

EXAMPLE 278

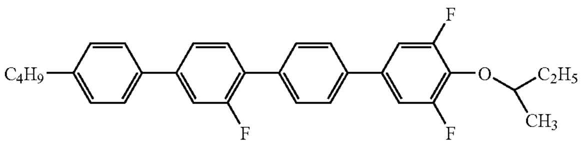

Phase transitions [° C.]: C 138 SmA 244 I

To a liquid-crystalline compound of the following formula:

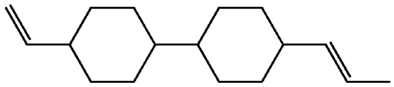

is added 1% by weight of the compound of Example 278, and the twisting power HTP of the composition is determined by the Grandjean-Cano method at 20° C. The composition has an HTP of 3.4.

EXAMPLE 279

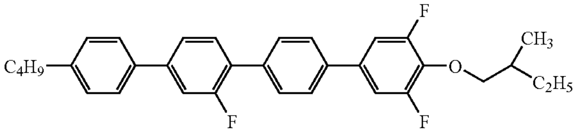

Phase transitions [° C.]: C 111 SmA 264 I

To a liquid-crystalline mixture which comprises the following compounds:

| | |
|---|---|
| 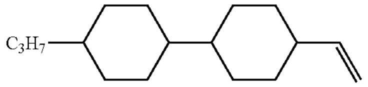 | 50% by weight |
| 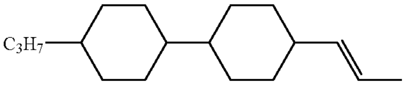 | 15% by weight |
| 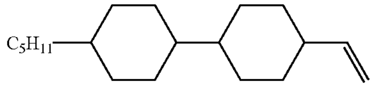 | 15% by weight |
| 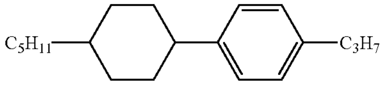 | 20% by weight |

is added 1% by weight of the compound of Example 279, and the twisting power HTP of the composition is determined by the Grandjean-Cano method at 20° C. The composition has an HTP of 6.3.

EXAMPLE 280

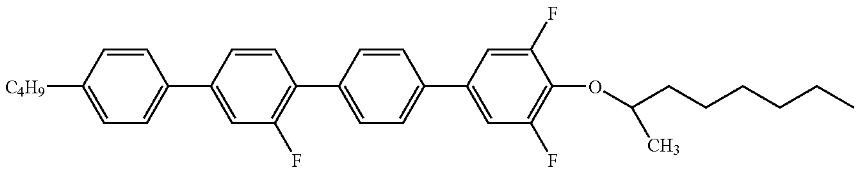

Phase transitions [° C.]: C 108 SmA 216 I

To a liquid-crystalline compound of the following formula:

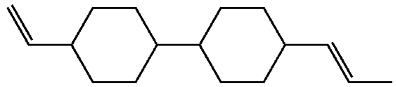

is added 1% by weight of the compound of Example 280, and the twisting power HTP of the composition is determined by the Grandjean-Cano method at 20° C. The composition has an HTP of 6.7.

EXAMPLE 281

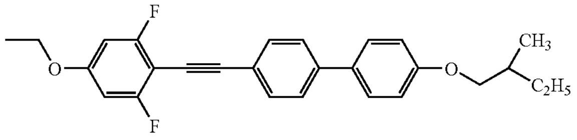

Phase transitions [° C.]: C 97 N 190.3 I

To a liquid-crystalline compound of the following formula:

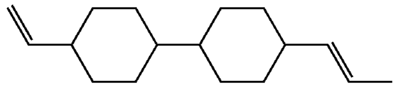

is added 1% by weight of the compound of Example 281, and the twisting power HTP of the composition is determined by the Grandjean-Cano method at 20° C. The composition has an HTP of 0.8.

EXAMPLE 282

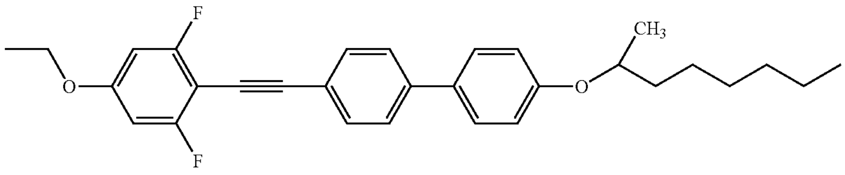

Phase transitions [° C.]: C 92 N 112 I

To a liquid-crystalline mixture as disclosed in Example 279 is added 1% by weight of the compound of Example 282, and the twisting power HTP of the composition is determined by the Grandjean-Cano method at 20° C. The composition has an HTP of 1.3.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A ring compound formula XIII:

XIII

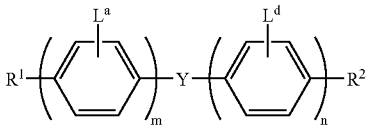

wherein m and n are each 1,

Y is a group selected from formulae XIV to XVII

XIV

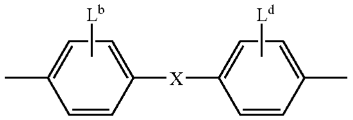

,

XV

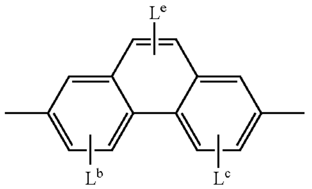

,

-continued

XVI

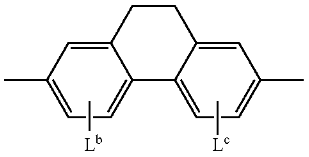

, and

XVII

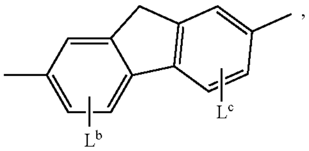

, wherein one or two CH groups in the aromatic ring systems may be replaced by N, X is a single bond, —$CH_2$—$CH_2$—, —CH═CH—, —C≡C— or

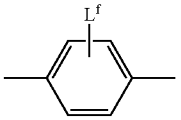

,

L, independently of one another, are identical or different and are R, F, Br, I, OH, OR, SH, SR, CN, $NO_2$, NO, CHO, COOH, COOR, $CONH_2$, CONHR, $CONR_2$, $CF_3$, $NH_2$, NHR or $NR_2$, R is an alkyl, alkenyl or acyl group having from 1 to 12 carbon atoms or an aryl group having 6 carbon atoms, which is optionally substituted by an alkyl group having from 1 to 12 carbon atoms, a, b, c, d, e and f, independently of one another, are identical or different and are 0, 1 or 2, and the sum (a+b+c+d+e+f) is 3 to 8, and $R^1$ and $R^2$, independently of one another, are identical or different and are H, F, Cl, CN, NCS, 2-oxapropyl, 2- or 3-oxabutyl, 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, a straight-chain or branched, optionally chiral, alkyl radical or alkoxy radical having from 1 to 12 carbon atoms or an alkenyl radical or alkynyl radical having from 2 to 8 carbon atoms.

2. A compound according to claim 1, wherein said compound is of formula XVIII

XVIII

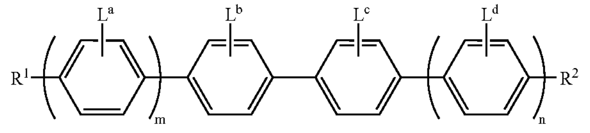

where m and n are each 1.

3. A compound according to claim 2, wherein $R^1$ and $R^2$, independently of one another, are identical or different and are each $C_1$-$C_7$-alkyl.

4. A compound according to claim 1, wherein X is a single bond.

5. A compound according to claim 1, wherein $R^1$ and $R^2$ are each, independently, H, F, Cl, CN, NCS, a straight-chain or branched, optionally chiral, alkyl radical or alkoxy radical having from 1 to 12 carbon atoms or an alkenyl radical or alkynyl radical having from 2 to 8 carbon atoms.

6. A compound according to claim 1, wherein L is in each case, independently of one another, F, $CF_3$ or $CH_3$.

7. A compound according to claim 1, wherein $R^2$ is a chiral alkyl radical having from 1 to 12 carbon atoms.

8. A compound according to claim 2, wherein said compound is of formula XVIIIf or XVIIIg:

XVIIIf

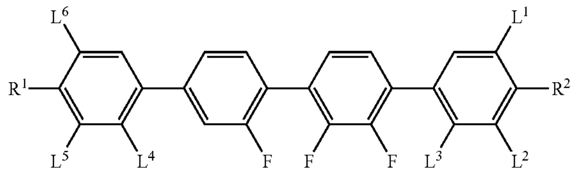

XVIIIg

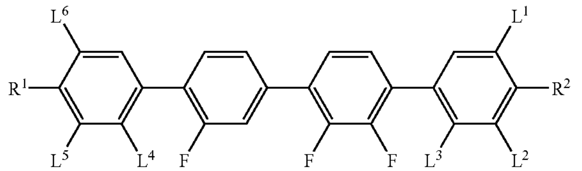

where $L^1$ to $L^6$ are each, independently of one another, R, F, Br, I, OH, OR, SH, SR, CN, $NO_2$, NO, CHO, COOH, COOR, $CONH_2$, CONHR, $CONR_2$, $CF_3$, $NH_2$, NHR or $NR_2$.

9. A compound according to claim 2, wherein L is in each case, independently of one another, F, $CF_3$ or $CH_3$.

10. A compound according to claim 8, wherein $L^1$ to $L^6$ are each, in each case independently of one another, F, $CF_3$ or $CH_3$.

11. A compound according to formula XVIII for XVIIIg:

XVIIIf

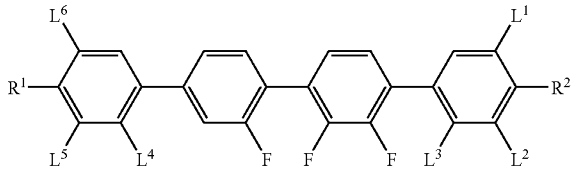

XVIIIg

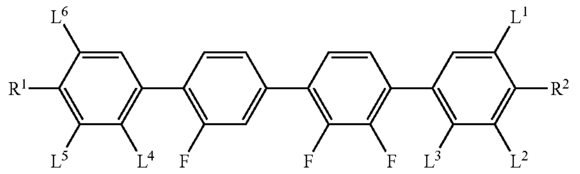

wherein $L^1$ to $L^6$ are each, independently of one another, R, F, Br, I, OH, OR, SH, SR, CN, $NO_2$, NO, CHO, COON, COOR, $CONH_2$, CONHR, $CONR_2$, $CF_3$, $NH_2$, NHR or $NR_2$;

$R^1$ is an alkyl, alkenyl or acyl group having from 1 to 12 carbon atoms or an aryl group having 6 carbon atoms, which is optionally substituted by an alkyl group having from 1 to 12 carbon atoms, $R^1$ and $R^2$, independently of one another, are identical or different and are H, F, Cl, CN, NCS, a straight-chain or branched, optionally chiral, alkyl radical or alkoxy radical having from 1 to 12 carbon atoms or an alkenyl radical or alkynyl radical having from 2 to 8 carbon atoms.

12. A compound according to claim 2, wherein $L^1$ to $L^6$ are each, in each case independently of one another, F, Cl, $CF_3$ or $CH_3$.

13. A compound of formula XVIII

XVIII

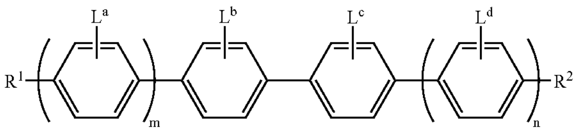

wherein m and n are each 1;

L is in each case, independently of one another, F, $CF_3$ or $CH_3$;

a, b, c, and d, independently of one another, are identical or different and are 0, 1 or 2, and the sum (a+b+c+d) is 3 to 8; and $R^1$ and $R_2$, independently of one another, are identical or different and are H, F, Cl, CN, NCS, a straight-chain or branched, optionally chiral, alkyl radical or alkoxy radical having from 1 to 12 carbon atoms or an alkenyl radical alkoxy radical having from 2 to 8 carbon atoms.

* * * * *

UNITED STATES PATENT AND TRADEMARK OFFICE

CERTIFICATE OF CORRECTION

PATENT NO. : 7,411,100 B2
APPLICATION NO. : 11/437608
DATED : August 12, 2008
INVENTOR(S) : Peter Baeuerle It is certified that error appears in the above-identified patent and that said Letters Patent is hereby corrected as shown below:

Column 48, line 1, reads “formula XVIII for” should read -- formula XVIIIf or --

Column 48, line 23, reads “COON,” should read -- COOH, --

Column 48, line 35, reads “according to claim 2,” should read -- according to claim 11, --

Column 48, line 59, reads “radical alkoxy radical” should read -- radical or alkynyl radical --

Signed and Sealed this

Thirtieth Day of December, 2008

JON W. DUDAS
*Director of the United States Patent and Trademark Office*